United States Patent
Houtzager et al.

(10) Patent No.: US 7,901,919 B2
(45) Date of Patent: *Mar. 8, 2011

(54) CHIMAERIC PHAGES

(75) Inventors: Erwin Houtzager, Amerongen (NL); Ton Logtenberg, Driebergen (NL); Cornelis Adriaan De Kruif, De Bilt (NL)

(73) Assignee: Crucell Holland B.V., Leiden (NL)

( * ) Notice: Subject to any disclaimer, the term of this patent is extended or adjusted under 35 U.S.C. 154(b) by 520 days.

This patent is subject to a terminal disclaimer.

(21) Appl. No.: 11/977,954

(22) Filed: Oct. 26, 2007

(65) Prior Publication Data

US 2009/0017521 A1    Jan. 15, 2009

Related U.S. Application Data

(62) Division of application No. 10/480,978, filed as application No. PCT/NL02/00391 on Jun. 14, 2002, now Pat. No. 7,329,530.

(30) Foreign Application Priority Data

Jun. 15, 2001 (EP) .................................... 01202304

(51) Int. Cl.
C12N 7/00 (2006.01)
C12N 7/01 (2006.01)
C12P 21/06 (2006.01)

(52) U.S. Cl. ............. 435/235.1; 435/5; 435/6; 435/69.1; 435/69.7; 536/23.4

(58) Field of Classification Search ............... 435/235.1, 435/5, 6, 7.1, 69.1, 69.4; 536/23.4
See application file for complete search history.

(56) References Cited

U.S. PATENT DOCUMENTS

| | | | |
|---|---|---|---|
| 6,027,930 A | 2/2000 | Borrebaeck | |
| 7,070,926 B2 | 7/2006 | Houtzager et al. | |
| 7,329,530 B2 | 2/2008 | Houtzager et al. | |
| 2003/0054495 A1 | 3/2003 | Houtzager et al. | |

FOREIGN PATENT DOCUMENTS

| | | |
|---|---|---|
| EP | 1 266 963 A1 | 12/2002 |
| WO | WO 02/103012 A1 | 12/2002 |

OTHER PUBLICATIONS

Rudert et al., A phage-based system to select multiple protein-protein interactions simultaneously from combinatorial libraries, FEBS Letters, 1998, pp. 135-140, vol. 440.
U.S. Appl. No. 12/589,181, filed Oct. 19, 2009, Logtenberg et al., Antibody Producing Non-Human Mammals.
U.S. Appl. No. 11/990,974, filed Feb. 21, 2008, Throsby et al., Method for Preparing Immunoglobulin Libraries.
U.S. Appl. No. 12/590,973, filed Nov. 16, 2009, ter Meulen et al., Binding Molecules Against SARS-Coronavirus and Uses Thereof.
U.S. Appl. No. 12/227,116, filed Nov. 7, 2008, Throsby et al., Human Binding Molecules Having Killing Activity Against Enterococci and Uses Thereof.
U.S. Appl. No. 12/227,029, filed Nov. 5, 2008, Throsby et al., Human Binding Molecules Having Killing Activity Against Staphylococci and Uses Thereof.
U.S. Appl. No. 12/310,812, filed Mar. 6, 2009, van den Brink et al., Human Binding Molecules Capable of Neutralizing Influenza Virus H5N1 and Uses Thereof.
U.S. Appl. No. 11/978,742, filed Oct. 29, 2007, Bakker et al., Binding Molecules Capable of Neutralizing Rabies Virus and Uses Thereof.
U.S. Appl. No. 11/980,237, filed Oct. 29, 2007, Bakker et al., Binding Molecules Capable of Neutralizing Rabies Virus and Uses Thereof.
U.S. Appl. No. 12/459,661, filed Jul. 6, 2009, Bakker et al., Binding Molecules Capable of Neutralizing Rabies Virus and Uses Thereof.
U.S. Appl. No. 11/919,265, filed Oct. 24, 2007, Throsby et al., Host Cell Specific Binding Molecules Capable of Neutralizing Viruses and Uses Thereof.
U.S. Appl. No. 11/922,405, filed Dec. 13, 2007, Throsby et al., Optimization of West Nile Virus Antibodies.
U.S. Appl. No. 12/459,285, filed Jun. 29, 2009, Houtzager et al., Antibody Producing Non-Human Mammals.
U.S. Appl. No. 12/221,021, filed Jul. 29, 2008, Van Berkel et al., Recombinant Production of Mixtures of Antibodies.
Balint et al., Antibody engineering by parsimonious mutagenesis, Gene, 1993, pp. 109-118, vol. 137.
Barbas III et al., In vitro evolution of a neutralizing human antibody to human immunodeficiency virus type 1 to enhance affinity and broaden strain cross-reactivity, Proc. Natl. Acad. Sci., Apr. 1994, pp. 3809-3813, vol. 91, USA.
Bass et al., Hormone Phage: An Enrichment Method for Variant Proteins With Altered Binding Properties, Proteins: Structure, Function, and Genetics, 1990, pp. 309-314, vol. 8.
Beekwilder et al., A phagemid vector using the *E. coli* phage shock promoter facilitates phage display of toxic proteins, Gene, 1999, pp. 23-31, vol. 228.
Berek et al., Mutation Drift and Repertoire Shift in the Maturation of the Immune Response, Immunological Reviews, 1987, pp. 23-41, No. 96.
Burton et al., Human Antibodies from Combinatorial Libraries, Advances in Immunology, pp. 191-280, vol. 57.
Chatellier et al., Interdomain interactions within the gene 3 protein of filamentous phage, FEBS Letters, 1999, pp. 371-374, vol. 463.
Crissman et al., Gene-III Protein of Filamentous Phages: Evidence for a Carboxyl-Terminal Domain with a Role in Morphogenesis, Virology, 1984, pp. 445-455, vol. 132.
Cwirla et al., Peptides on phage: A vast library of peptides for identifying ligands, Proc. Natl. Acad. Sci., Aug. 1990, pp. 6378-6382, vol. 87.
De Kruif et al., Selection and Application of Human Single Chain Fv Antibody Fragments from a Semi-synthetic Phage Antibody Display Library with Designed CDR3 Regions, J. Mol. Biol., 1995, pp. 97-105, vol. 248.

(Continued)

*Primary Examiner* — Maria Leavitt
(74) *Attorney, Agent, or Firm* — TraskBritt, P.C.

(57) ABSTRACT

The invention relates to the field of generating helper phages and phage display libraries for the identification of binding molecules. The invention provide chimaeric phages having a coat comprising a protein mixture. The protein mixture comprises a fusion protein having a proteinaceous molecule fused to a functional form of a phage coat protein and a mutant form of the phage coat protein, wherein the mutant form is impaired in binding to a host cell receptor. The invention further provides new phage collections, novel helper phages and methods and means for producing chimaeric phages, infectious phages and helper phages.

8 Claims, 17 Drawing Sheets

OTHER PUBLICATIONS

De Kruif et al., Rapid selection of cell subpopulation-specific human monoclonal antibodies from a synthetic phage antibody library, Proc. Natl. Acad. Sci., Apr. 1995, pp. 3938-3942, vol. 92, USA.

Deng et al., Interaction of the Globular Domains of pIII Protein of Filamentous Bacteriophage fd with the F-Pilus of *Escherichia coli*, Virology, 1999, pp. 271-277, vol. 253.

Devlin et al., Random Peptide Libraries: A Source of Specific Protein Binding Molecules, Science, Jul. 27, 1990, pp. 404-406, vol. 249.

Duenas et al., Clonal Selection and Amplification of Phage Displayed Antibodies by Linking Antigen Recognition and Phage Replication, Bio/Technology, Oct. 1994, pp. 999-1002, vol. 12.

Duenas et al., Novel helper phage design: intergenic region affects the assembly of bacteriophages and the size of antibody libraries, FEMS Microbiology Letters, 1995, pp. 317-322, vol. 125.

Felici et al., Mimicking of discontinuous epitopes by phage-displayed peptides, II. Selection of clones recognized by a protective monoclonal antibody against the *Bordetella pertussis* toxin from phage peptide libraries, Gene, 1993, pp. 21-27, vol. 128.

Jestin et al., Improving the display of proteins on filamentous phage, Res. Microbiology, Mar. 2001, pp. 187-191, vol. 152, No. 2.

Hawkins et al., Selection of Phage Antibodies by Binding Affinity, Mimicking Affinity Maturation, J. Mol. Biol., 1992, pp. 889-896, vol. 226.

Holliger et al., A conserved infection pathway for filamentous bacteriophages is suggested by the structure of the membrane penetration domain of the minor coat protein g3p from phage fd, Structure, 1997, pp. 265-275, vol. 5, No. 2.

Hoogenboom et al., Designing and optimizing library selection strategies for generating high-affinity antibodies, TIB Tech, Feb. 1997, pp. 62-70, vol. 15.

Krebber et al., Co-selection of cognate antibody—antigen pairs by selectively-infective phages, FEBS Letters, 1995, pp. 227-231, vol. 377.

Krebber et al., Selectively-infective Phage (SIP): A Mechanistic Dissection of a Novel in vivo Selection for Protein-ligand Interactions, J. Mol. Biol. 1997, pp. 607-618, vol. 268.

Kristensen et al., Proteolytic selection for protein folding using filamentous bacteriophages, Folding & Design, pp. 321-328, vol. 3, No. 5.

Low et al., Mimicking Somatic Hypermutation: Affinity Maturation of Antibodies Displayed on Bacteriophage Using a Bacterial Mutator Strain, J. Mol. Biol., 1996, pp. 359-368, vol. 260.

Lubkowski et al., The structural basis of phage display elucidated by the crystal structure of the N-terminal domains of g3p, Nature Structural Biology, Feb. 1998, pp. 140-147, vol. 5, No. 2.

Lubkowski et al., Filamentous phage infection: crystal structure of g3p in complex with its coreceptor, the C-terminal domain of TolA, Structure, 1999, pp. 711-722, vol. 7, No. 6.

Luzzago et al., Mimicking of discontinuous epitopes by phage-displayed peptides, I. Epitope mapping of human H ferritin using a phage library of constrained peptides, Gene, 1993, pp. 51-57, vol. 128.

Lopez et al., Morphogenesis of Filamentous Bacteriophage f1: Orientation of Extrusion and Production of Polyphage, Virology, 1983, pp. 177-193, vol. 127.

Model et al., The *Escherichia coli* phage-shock-protein (psp) operon, Molecular Microbiology, 1997, pp. 255-261, vol. 24, No. 2.

Moody et al., Geometry of Phage Head Construction, Journal of Molecular Biology, 1999, pp. 401-433, vol. 293.

Nelson et al., Filamentous Phage DNA Cloning Vectors: A Noninfective Mutant with a Nonpolar Deletion in Gene III, Virology, 1981, pp. 338-350, vol. 108.

Nilsson et al., The Phage Infection Process: a Functional Role for the Distal Linker Region of Bacteriophage Protein 3, Journal of Virology, May 2000, pp. 4229-4235, vol. 74.

Pratt et al., Conditional Lethal Mutants of the Small Filamentous Coliphage M13. II. Two Genes for Coat Proteins, Virology, 1969, pp. 42-53, vol. 39.

Rakonjac et al., Filamentous phage infection-mediated gene expression: construction and propagation of the gIII deletion mutant helper phage R408d3, Gene, 1997, pp. 99-103, vol. 198.

Rakonjac et al., Roles of pIII in Filamentous Phage Assembly, J. Mol. Biol. 1998, pp. 25-41, vol. 282.

Riechmann et al., The C-Terminal Domain of TolA Is the Coreceptor of Filamentous Phage Infection of *E. coli*, Cell, Jul. 25, 1997, pp. 351-360, vol. 90.

Rondot et al., A helper phage to improve single-chain antibody presentation in phage display, Nature Biotech, pp. 75-78, vol. 19.

Russel et al., Genetic Analysis of the Filamentous Bacteriophage Packaging Signal and of the Proteins That Interact with It, Journal of Virology, Aug. 1989, pp. 3284-3295, vol. 63, No. 8.

Smith, Filamentous Fusion Phage: Novel Expression Vectors That Display Cloned Antigens on the Virion Surface, Science, Jun. 14, 1985, pp. 1315-1317, vol. 228.

Spada et al., Selectively Infective Phages (SIP), Biol. Chem., Jun. 1997, pp. 445-456, vol. 378.

Vaughan et al., Human antibodies by design, Nature Biotechnology, Jun. 1998, pp. 535-539, vol. 16.

Winter et al., Man-made antibodies, Nature, Jan. 24, 1991, pp. 293-299, vol. 349.

Yang et al., CDR Walking Mutagenesis for the Affinity Maturation of a Potent Human Anti-HIV-1 Antibody into the Picomolar Range, J. Mol. Biol., 1995, pp. 392-403.

PCT International Search Report, PCT/NL02/00391, dated Nov. 25, 2002, 3 pages.

PCT International Preliminary Examination Report, PCT/NL02/00391, dated Sep. 4, 2003, 5 pages.

```
   1 TGCCTGACTCCCCGTCGTGTAGATAACTACGATACGGGAGGGCTTACCATCTGGCCTGCAATGATACCGCGAGACCCACGCTCACCGGCTCCA
 101 GATTTATCAGCAATAACCAGCCAGCTGGCAAGATCGAGCTCGCCCGGGATCGACCAGTTGTGATTTGCTTTGAACTTTGTCTTGCACGACGGTCTGCGTTG
 201 TCGGGAAGATGCTGATCCTCAACTCAGCAAAGTTCGATTTATTCAACAAAGCCGCCGTCCCGTCAAGTCTAATGCTCTGCCAGTGTTA
 301 CAACCAATTAACCAATTCTGATTAGAAAAACTCATCGAGCATCAAATGAAAACTGCAATTATTCATATCAGGATTATCAATACCATATTTTGAAAAAGC
 401 CGTTTCTGTAATGAAGGAGAAAACTCACCGAGGCAGTTCCATAGGATGCAAGATCCTGTATCGGTCTGCGATTCCGACTCGTCCAACATCAATACAAC
                                                                                                HindIII
 501 CTATTAATTTCCCCTCGTCAAAAATAAGGTTATCAACGTGAGAAATCACCATGAGTGACGACTGAATCCGTGAGAATGCAAAGCTTATGCATTTCTTT
 601 CCAGACTTGTTCAACAGGCCAGCCATTACGCTCGTCATCAAAAATCACTCGCATCGTCAACAACCGTTATTCATTCGTGATTGCGCCTGAGCGAGACGAAAT
 701 ACGCGATCGCTGTTAAAGGACAATTACAAACAGGAATCGAATGCAACCGGCGCAGGAGAACACTGCAACCATGCCAGGAGTACGATCAACATATTTCACCTGAATCAGAT
 801 ATTCTTCTAATACCTGGAATGCTGTTTCCGGATCGCAGTGTGTGAGTAACATCATCAGGAGTAATCAGCCCTTGCAACGTTGCATGTTGATGGTCGGAAGAGG
 901 CATAAATTCCGTCAGCCAGTTTAGTCTGACAATCCATCGTAACATCATTGGCAACGCCATTTATACCGAGCCAATCATTGCGAGCATCAGCTTTATTGTTCATGATGATTAATCGCG
1001 TTCCCATACAATCGATAGATTGTCGCACCTGATTGCCCGAGCCCCATAATCCCTTGAATGGCTCATAATGCGCGAGCCATAATCAGCAGTTTATTGCATGATGAAATCGCG
1101 GCCTCGAGCAAGACGTTTCCCGTTGAATATGGCTCATAACACAACGTGGCTTTCCCCCCTGCGATTTTACGAGTCTCGGCAGGTCTCGGCCTATTCTTTTGATTTATAAGGGATTT
1201 ATCTTGTGCAATGCAATCAGAGATTTTGAAACACAACGTGATTTATCAACGGGTACATGCAGTTTTTAACGATTGACATGCTAGTTTCACGATTACCGTCATCGATTCTCTTGTTGC
1301 TGCCGATTTCGGCCTATTGTTTTTGGGGCTTTCTGATAGCCCTTTCTGATAGCCTTTCTCACCCTTTTGAATCTTTACAGGCATTGTTTTGGTACAACCGATTCATGCATTTAACGATATATGC
1401 TACAATCTTTCTGTTTTCCTTATTATCAACCGGGTACCTCTCAAAAGTATTACAGGTCATAATGTTTTGTACAACCGATTTGCATTTAAAATATATGAGGGTTCTAAAAA
1501 TCCAGACTCTCAGGCAATGACTGTCTCCGGCAATGACCTTTTGAATCTTTTACAGGTCATAATGTTTTGTACAACCGATTTGCATTTAAAATATATGAGGGTTCTAAAAA
1601 TTGATGGTGATTTTGACTTCCTTAGCGTTAGCGTTGCTATACCTTTACAGGCTTCATTAATGTTTTGTACAACCGATTTTATGCTTCAGCTCGGCGCC
1701 TTTTTATCCTTGCGTTAATTCTTTTGCCTTTGCCTGACCATTTGCAATCTCTAATCCTGACCGTTGGAGTTTGCTTCGACTATAATAGTCAGGTGAACGTCTGATCAGCAATTAAGCTCAACTGTTAC
1801 CAAATGAAAAATATAGCTAAAACAGGTTATTGACCAACACCCTATTGCAAATTAAAACATGTTGAGCTACGACATTATAATCCTGACCGTTGGAGTTTGCTTCGACTATAATAGTCAGGTGAACGTCTGATCAGCAATTAAGCTCAACTGTTAC
1901 GTCATTCGTTTTCTGCTCGGCAAACTGTTTAAACCATTGAAGGGACCTACTCCATTAGTTGACATCGCTAAATTTGACGGTATTCCGTCTAAATCTGATGAATCCGCAGTATTGGACGTCATTGGACGCTATCCAGTCTAAACATTTT
2001 ATGGAATGAAAACTTCCCAGACACCGAGCTTCGGGCTTCCTCTAATGTTAGTTGACTACTTGTTAAAGGTACTCTGTTAATCTTTTTGATGCAATCCTGATCAGGAATAAGGTTCTCGATTATGGCAATTAAAACGC
2101 ATGACCTCTTGAAGTCTTTCGGCTCTTCGGCTTCCAGAAGGCTTCAATGAAACGTTGCTTCGCCGCTTATACAGCTTCAGGTAAACGACCGTATCAGTTCGACGTCTAAACGACCGTATCAGTTCGACGTCTAAACGTTTGTATTAAAGACTCGGAAGCTCGAATTAAAACGC
2201 GATATTGAAGTCTTTCGGGCTTCCTCTAATGCTTCCAGAAGGCTTCAATGAAACGTTGCTTCGCCGCTTATACAGCTTCAGGTAAACGACCGTATCAGTTGGACGTAAACCTGATTTTTGATTTATG
2301 GTCATTCGTTTCTGCAACTGTTAAACTTCTTTGGCGTTGAACTGTATGCGTTGCAAAACTCTTTCGGCGGTTGCTTCAATAATCCAAAACGTCTTTAGACTTCAAGCTTAAACCGTTCTAACCAGTCAGATAGTTGCTCTTA
2401 ACTATTACCCGTCTAATTCTTGGCAAACTGTTTGGCGTTGAACTTCTTTGGCGTTATCTCGCTTGCAAAACTCTTTCGGCGGTTGCTTCAATAATCCAAAACGTCTTTAGACTTCAAGCTTAAACCGTTCTAACCAGTCAGATAGTTGCTCTTA
2501 CTATGCCTCGTAATTCTTTGGCGTTATATCGCTTGTCAAGATTTCTTGTCTTAAACATCGTATATATCCTAAAATGCTGACTGGGTAATTGGTATTCACTCACTGATCACAACCAATGATTA
2601 TCCGTTAGTTCGTTTTATTAACGTAGATTTTTTCCTCCCAACGTCTCGACTCCGTTGGTATTCTGCTGAATGCCAGTTCTTAAATATGCCATAAGGTAATTCACAATGATTA
2701 AAGTTGAAATTAAACCATCCAAGCCAATTTCTTGTCAAGTATCCAAGCCATCGGTAGCCAGAGCCAGTCAAGCCTTCATGAACCAGGGTATTGACGCTTGTTCCTCTTA
2801 TTTGGGTAATGAATATCCGGTTTCGCGACCCCCCCGATCAACGGGGGTTGTTCAAGCCCTATGATGGTAGCCGTTCGCCTATGATGGTAACATGGGAGCAGCTTGTCGCCGATTTTCATCTGTCCTTCTTCAAA
2901 GTTGGTCAGTTGCGTAATTCTTGCAAGCCCCTGCCGCTGCAGGTCGCGCCAGGTCGTGTTTTTAGTGTATTCGTTGGGGTATTCTTTTCGCCTCTGTTCGTTTTAGTTG
3001 ATACAAATCTCCGTTGACTTTCTTTGTTCCGCCGTTGGTTATAATCGCTGTTGGGTATTCTTTTCGCCTCTGTTCGTTTTAGTTG
                 SnaBI 3101 GTGCCTTCGTAGTGCATTACGTATTTACCCGTTAATGAAACTTCCTCATGAAAAAGTCTTTAGTCCTCAAAGCCTCTGCTACCCTG
3201 TTCCGATGCTGTCTTTCGCTGCTGCTGAGGGTGACGATCCCGCAAAAGCGGCCTTTAACTCCCTGCAAGCCTCAGCGACCGAATATCGGTTATGCGTGGGC
```

FIG. 6B

```
3301 GATGGTGTGTGTCATTGTCGGCGCAACTATCGGTATCAAGCTGTGTTAAGGAAATTCACCCTGAAAGCAAGCTGTGATAAACCGATACAATTAAAGGCTCCTTT
             V  K  K  L  F  A  I  P  L  V  V  P  F  Y  S  H  S  A  E  T  V  E  S
3401 TGGAGCCTTTTTTTTGGAGATTTCAACGTGAAAAATTATTCGCAATTCCTTAGTTGTTCCTTTCTATTCTCACTCCGCTGAAACTGTTGAAAG
       C  L  A  K  P  H  T  E  N  S  F  T  N  V  W  K  D  D  K  T  L  D  R  Y  A  N  Y  E  G  C  L  W  N
3501 TTGTTTAGCAAAACCCCATACAGAAAATTCATTACTAACGTCTGGAAAGACGACAAAACTTTAGATCGTTACGTTAACTATGAGGGCTGTCTGTGGAAT
     A  T  G  V  V  C  T  G  D  E  T  Q  C  Y  G  T  W  V  P  I  G  L  A  I  P  E  N  E  G  G  G  S
3601 GCTACAGGCGTTGTAGTTTGTACTGGTGACGAAACTCAGTGTTACGGTACAACTGGGTTCCTATTGGGCTTGCTATCCTGAAAATGAGGGTGGCTCTG
     E  G  G  S  E  G  G  S  E  G  G  S  E  G  G  S  T  K  P  P  E  Y  G  D  T  P  I  P  G  Y  T  I  N  P  L
3701 AGGGTGGCGGTTCTGAGGGTGGCGGTTCTGAGGGTGGCGGTTCTGAGGGTGGCGGTACTAAACCTCCTGAGTACGGTGATACACCTATTCCGGGCTATACTATCAACCCTCT
     D  G  T  Y  P  P  G  T  E  Q  N  P  A  N  P  S  L  E  E  S  Q  P  L  N  T  F  M  F  Q  N  N
3801 CGACGGCACTTATCCGCCTGGTACTGAGCAAAACCCCGCTAATCCTTCTCTTGAGGAGTCTCAGCCTCTTAATACTTTCATGTTTCAGAATAAT
     R  F  R  N  R  Q  G  A  L  T  V  Y  T  G  T  V  T  Q  G  T  D  P  V  K  T  Y  Y  Q  Y  T  P  V  S
3901 AGGTTCCGAAATAGGCAGGGGCATTAACTGTTTATACGGGCACTGTTACTCAAGGCACTGACCCCGTTAAAACTTATTACCAGTACACTCCTGTATCAT
                                                                                                        BamHI
4001 S  K  A  M  Y  D  A  Y  W  N  G  K  F  R  D  C  A  F  H  S  G  F  N  E  D  P  F  V  C  E  Y  Q  G  Q
     CAAAAGCCATGTATGACGCTTACTGGAACGGTAAATTCAGAGACTGCGCTTTCCATTCTGGCTTTAATGAGGATCCATTCGTTTGTGAATATCAAGGCCA
4101  S  S  D  L  P  Q  P  P  V  N  A  G  G  G  S  G  G  G  S  G  G  G  S  E  G  G  S  E  G  G  G  S
     ATCGTCTGACCTGCCTCAACCTCCTGTTAATGCTGGCGGCGGCTCTGGTGGTTCTGGTGGCGGTTCTGAGGGTGGCGGTTCTGAGGGTGGCGGTTCT
4201  E  G  G  S  E  G  G  G  S  G  E  G  G  S  G  D  F  D  Y  E  K  M  A  N  A  N  K  G  A  M  T
     GAGGGTGGCGGCTCTGAGGGAGGCGGTTCCGGTGGCGGCTCTGAGGGAGGCAGTCTGGTGATTTGATTATGAAAGATGCAAACGCTAATAAGGGGCTATGACCG
4301  E  N  A  D  E  N  A  L  Q  S  D  A  K  G  K  L  D  S  V  A  T  D  Y  G  A  A  I  D  G  F  I  G  D  V
     AAAATGCCGATGAAAACGCCTACAGTCTGGACGCTAAAGGCAAACTTGATTCTGTGCTACTGATTACGGTGCTGCTATCGATGGTTTCATTGGTGACGT
4401  S  G  L  A  N  G  N  G  A  T  G  D  F  A  G  S  N  S  Q  M  A  Q  V  G  D  G  D  N  S  P  L  M  N
     TTCCGGCCTTGCTAATGGTAATGGTGCTACTGGTGACTTTGCTGGCTCTAATTCCCAAATGCTTCAAGTCGGTGACGGTGATAATTCACCTTTAATGAAT
4501  N  F  R  Q  Y  L  P  S  L  P  Q  S  V  E  C  R  P  F  V  F  G  A  G  K  P  Y  E  F  S  I  D  C  D
     AATTTCCGTCAATATTTACCTTCCCTCCCTCAATCGGTTGAATGCCGTCCTTTTGTCTTTGGCGCTGGTAAACCATATGAATTTTCTATTGATTGTGACA
4601  K  I  N  L  F  R  G  V  F  A  F  L  L  Y  V  A  T  F  M  Y  V  F  S  T  F  A  N  I  L  R  N  K  E  S
     AAATAAACTTATTCCGTGGTGTCTTTGCGTTTCTTTTATATGTTGCCACCTTTATGTATGTATTTCTCCTAACATACGTTGCTAACATACTGCGTAATAAGGAGTC
4701  .  *
     TTAATCATGCCAGTTCTTTTGGGTATTCCGTTATTATTGCGTTCCTTCCTCGGTAACTTTGTTCGGCTATCTGCTTACTTTTCTTAAAAAGG
4801 GCTTCGGTAAGATAGCTATTGCTATTTCATTGTTTCTTGCTCTTATTATTGGGCTTAACTCAATTCTTGTGGGTTATCTCTCTGATATTAGCGCTCAATT
4901 ACCCTCTGACTTTGTTCAGGGTGTTCAGTTAATTCTCCCGTCTAATGCTTCCCTGTGTTTATGGCTTCTGGTGGGTTCCTCAATCGCCGGTTAGCTT
5001 GACGTTAAACAAAATCGTTTCTTATTTGGATTGGGATGATCAAATATCTTGTAAATCGCTCAAATAAATTTTAAGGCTTCAAAAACTCCCGCAAGTCGGTTGCC
5101 GTTGGTAAGATTCAGGATGGGATGTGCGGAAAATTGTAGCTGGGCGATAAGCTTCTATATCGATTTCCTTGCTATTGGGCCGATCGGGAGGTTCGTAAAA
5201 CGGCTCGGCGTTCTAGAATACCGGATACCAGATTGCGATAAGGAAAGACAGCGCCGATTATTGATTGTTCTACATCGCTCTAAAACGGCTTGCT
5301 TGTTCTCGATGAGTGCGGTACTTGGTTTAATACCGGTTCTTGGAATGATAAGAAAGACAGCGCCGATTATTGATTGTTCTACATCGCTCTAAATTAGGA
```

G3-minus protein

GGTTATGCGTGGGCGATGGTTGTTGTCATTGTCGGCGCAACTATCGGTATCAAGCTGTTAAGAAATTCACCTCG
AAAGCAAGCTGATAAACCGATAACAATTAAAGGCTCCTTTTGGAGCCTTTTTTTGGAGATTTCAACAAGCTTC
TGCCGTAATAAGGAGTCT*TAATCATGCCAGTTCTTCTTTTGGGTATTCCGTTATTATTGCGTTTCCTCGGTTTCCTTCT
GGTAACTTTGTTCGGCTATCTGCTAACTTTTCTTAAAAGG

FIG. 6D

D3 domain of g3 Protein

```
TTGACTCCCTGCAAGCCTCAGCGACCGAATATATCGGTTATGCGTGGGCGATGGTTGTTGTCATTGTCGGCGCAA
CTATCGGTATCAAGCTGTTAAGAAATTCACCTCGAAAGCAAGCTGATAAACGATACAATTAAAGGCTCCTTTT
GGAGCCTTTTTTGGAGAGATTTCAACGTGAAAAAATTATTATTCGCAATTCCTTAGTGTTCCTTCTATTC
TCACTCCGCTGGATCCTCTGGTTCCGGTGATTTGATTATGAAAATATGGCAAACGCTAATAAGGGGCTATGAC
CGAAATGCCGATGAAACGCGACAGTCTGACGCTAAAGGCAAACTTGATTCTGTCGCTACTGATTACGGTGC
TGCTATCGACGGTTTCATTGGCTCAAGTCGGTGACGTGGACCGGTGATAATTCACCTTTAATGAATAATTCCGTCAATATTACCTTC
TAATTCCCAAATGGCTCAAGTCGGTGACGTGAATGTGCGCCCCTTTGCGTCTTCTTTATATGTTGCCACCTTTATATGTATGTATTATTGCGTTTCCTC
CCTTCCTCAATCGGTGGTGTTATTCCGTGGTGTCTTTTTGCGTGTCTTTATGTTGCCACCTTTATATGTATGTATTATTGCGTTTCCTC
CAAAATAAACTTATTCCGTGGTGTTATTCCGTGGTAACCATATGTTGCCACCTTTATATGTATGTATTATTGCGTTTCCTC
TGCTAACATACTGCGTAATAAGGAGTCTTCATGCCAGTTCTTTTGGTATTCCGTTATTATTCCGTTATTATTGCGTTTCCTC
GGTTTCCTTCGGTAACTTTGTTCGCGTAATCGCTAACTTTGTTCTTAAAAGGGCTTCGGTAAGATAGCTATTGCT
ATTTCAT
```

FIG. 7B

| | |
|---|---|
| A | GCG GCA GCC GCT |
| C | TGC TGT |
| D | GAT GAC |
| E | GAA GAG |
| F | TTT TTC |
| G | GGT GGC |
| H | CAT CAC |
| I | ATT ATC ATG |
| K | AAA |
| L | CTG |
| M | ATG |
| N | AAC AAT |
| P | CCG |
| Q | CAG |
| R | CGT CGC |
| S | AGC TCT |
| T | ACC ACG |
| V | GTG GTT GTC |
| W | TGG |
| Y | TAT TAC |
| STOP | TAA TGA |

FIG. 8

SEQUENCE LISTING

<160> NUMBER OF SEQ ID NOS: 19

<210> SEQ ID NO 1
<211> LENGTH: 31
<212> TYPE: DNA
<213> ORGANISM: Artificial
<220> FEATURE:
<223> OTHER INFORMATION: PCR Primer

<400> SEQUENCE: 1
ggatcctctg gttccggtga ttttgattat g                                31

<210> SEQ ID NO 2
<211> LENGTH: 30
<212> TYPE: DNA
<213> ORGANISM: Artificial
<220> FEATURE:
<223> OTHER INFORMATION: PCR Primer

<400> SEQUENCE: 2
ggatccagcg gagtgagaat agaaaggaac                                  30

<210> SEQ ID NO 3
<211> LENGTH: 33
<212> TYPE: DNA
<213> ORGANISM: Artificial
<220> FEATURE:
<223> OTHER INFORMATION: PCR Primer

<400> SEQUENCE: 3
aagcttctgc gtaataagga gtcttaatca tgc                              33

<210> SEQ ID NO 4
<211> LENGTH: 30
<212> TYPE: DNA
<213> ORGANISM: Artificial
<220> FEATURE:
<223> OTHER INFORMATION: PCR Primer

<400> SEQUENCE: 4
aagcttgttg aaaatctcca aaaaaaagc                                   30

<210> SEQ ID NO 5
<211> LENGTH: 31
<212> TYPE: DNA
<213> ORGANISM: Artificial
<220> FEATURE:
<223> OTHER INFORMATION: PCR Primer

<400> SEQUENCE: 5
ccatggctga aactgttgaa agttgtttag c                                31

<210> SEQ ID NO 6
<211> LENGTH: 31
<212> TYPE: DNA
<213> ORGANISM: Artificial
<220> FEATURE:
<223> OTHER INFORMATION: PCR Primer

<400> SEQUENCE: 6
tctagattaa gactccttat tacgcagtat g                                31

<210> SEQ ID NO 7
<211> LENGTH: 20
<212> TYPE: DNA

```
<213> ORGANISM: Artificial
<220> FEATURE:
<223> OTHER INFORMATION: PCR Primer

<400> SEQUENCE: 7
ttaggttggt gccttcgtag                                                    20

<210> SEQ ID NO 8
<211> LENGTH: 27
<212> TYPE: DNA
<213> ORGANISM: Artificial
<220> FEATURE:
<223> OTHER INFORMATION: PCR Primer

<400> SEQUENCE: 8
ggatccagcg gagtgagaat agaaagg                                            27

<210> SEQ ID NO 9
<211> LENGTH: 29
<212> TYPE: DNA
<213> ORGANISM: Artificial
<220> FEATURE:
<223> OTHER INFORMATION: PCR Primer

<400> SEQUENCE: 9
agatctggta ctaaacctcc tgagtacgg                                          29

<210> SEQ ID NO 10
<211> LENGTH: 31
<212> TYPE: DNA
<213> ORGANISM: Artificial
<220> FEATURE:
<223> OTHER INFORMATION: PCR Primer

<400> SEQUENCE: 10
ggatcctctg gttccggtga ttttgattat g                                       31

<210> SEQ ID NO 11
<211> LENGTH: 20
<212> TYPE: DNA
<213> ORGANISM: Artificial
<220> FEATURE:
<223> OTHER INFORMATION: PCR Primer

<400> SEQUENCE: 11
ttgcttctgt aaatcgtcgc                                                    20

<210> SEQ ID NO 12
<211> LENGTH: 59
<212> TYPE: DNA
<213> ORGANISM: Artificial
<220> FEATURE:
<223> OTHER INFORMATION: PCR Primer

<400> SEQUENCE: 12
caaattctat ttcaaggaga cagtcataat gaaaaaatta ttattcgcaa ttcctttag         59

<210> SEQ ID NO 13
<211> LENGTH: 40
<212> TYPE: DNA
<213> ORGANISM: Artificial
<220> FEATURE:
<223> OTHER INFORMATION: PCR Primer

<400> SEQUENCE: 13
gattacgcca agcttgcatg caaattctat ttcaaggaga                              40
```

```
<210> SEQ ID NO 14
<211> LENGTH: 45
<212> TYPE: DNA
<213> ORGANISM: Artificial
<220> FEATURE:
<223> OTHER INFORMATION: PCR Primer

<400> SEQUENCE: 14
gctaacatac tgcgtaataa ggagtcttaa gaattccagt tcttt             45

<210> SEQ ID NO 15
<211> LENGTH: 8668
<212> TYPE: DNA
<213> ORGANISM: VCSM13 Helper Phage

<400> SEQUENCE: 15
tgcctgactc cccgtcgtgt agataactac gatacgggag ggcttaccat ctggccccag    60
tgctgcaatg ataccgcgag acccacgctc accggctcca gatttatcag caataaacca   120
gccagccgat tcgagctcgc cggggatcg accagttggt gattttgaac ttttgctttg    180
ccacggaacg gtctgcgttg tcgggaagat gcgtgatctg atccttcaac tcagcaaaag   240
ttcgatttat tcaacaaagc cgccgtcccg tcaagtcagc gtaatgctct gccagtgtta   300
caaccaatta accaattctg attagaaaaa ctcatcgagc atcaaatgaa actgcaattt   360
attcatatca ggattatcaa taccatattt tgaaaaagc cgtttctgta atgaaggaga    420
aaactcaccg aggcagttcc ataggatggc aagatcctgg tatcggtctg cgattccgac   480
tcgtccaaca tcaatacaac ctattaattt cccctcgtca aaataaggt tatcaagtga    540 gaaatcacca tgagtgacga ctgaatccgg tgagaatggc aaaagcttat gcatttcttt   600
ccagacttgt tcaacaggcc agccattacg ctcgtcatca aaatcactcg catcaaccaa   660
accgttattc attcgtgatt gcgcctgagc gagacgaaat acgcgatcgc tgttaaaagg   720
acaattacaa acaggaatcg aatgcaaccg gcgcaggaac actgccagcg catcaacaat   780
attttcacct gaatcaggat attcttctaa tacctggaat gctgttttcc cggggatcgc   840
agtggtgagt aaccatgcat catcaggagt acggataaaa tgcttgatgg tcggaagagg   900
cataaattcc gtcagccagt ttagtctgac catctcatct gtaacatcat tggcaacgct   960
acctttgcca tgtttcagaa acaactctgg cgcatcgggc ttcccataca atcgatagat  1020
tgtcgcacct gattgcccga cattatcgcg agcccattta tacccatata atcagcatc   1080 catgttggaa tttaatcgcg gcctcgagca agacgtttcc cgttgaatat ggctcataac  1140 ccccttgta ttactgttta tgtaagcaga cagttttatt gttcatgatg atatatttt    1200 atcttgtgca atgtaaacatc agagattttg aaacacaacg tggctttccc ccccccccc  1260 ctgcaggtct cggctattc ttttgattta aagggatt tgccgatttc ggcctattgg    1320
ttaaaaaatg agctgattta acaaaaattt aacgcgaatt ttaacaaaat attaacgttt   1380
acaatttaaa tatttgctta tacaatcttc ctgttttgg ggcttttctt attatcaacc   1440
ggggtacata tgattgacat gctagtttta cgattaccgt tcatcgattc tcttgtttgc   1500
tccagactct caggcaatga cctgatagcc tttgtagacc tctcaaaaat agctaccctc   1560
tccggcatga atttatcagc tagaacggtt gaatatcatg ttgatggtga tttgactgtc   1620
tccggccttt ctcacccttt tgaatcttta cctacacatt actcaggcat tgcatttaaa   1680
atatatgagg gttctaaaaa tttttatcct tgcgttgaaa taaaggcttc tcccgcaaaa   1740
gtattacagg gtcataatgt ttttggtaca accgatttag ctttatgctc tgaggcttta   1800
```

```
ttgcttaatt ttgctaattc tttgccttgc ctgtatgatt tattggatgt taacgctact    1860
actattagta gaattgatgc caccttttca gctcgcgccc caaatgaaaa tatagctaaa    1920
caggttattg accatttgcg aaatgtatct aatggtcaaa ctaaatctac tcgttcgcag    1980
aattgggaat caactgttac atggaatgaa acttccagac accgtacttt agttgcatat    2040
ttaaaacatg ttgagctaca gcaccagatt cagcaattaa gctctaagcc atccgcaaaa    2100
atgacctctt atcaaaagga gcaattaaag gtactctcta atcctgacct gttggagttt    2160
gcttccggtc tggttcgctt tgaagctcga attaaaacgc gatatttgaa gtctttcggg    2220
cttcctctta atcttttttga tgcaatccgc tttgcttctg actataatag tcagggtaaa    2280
gacctgattt ttgatttatg gtcattctcg ttttctgaac tgtttaaacg atttgagggg    2340
gattcaatga atatttatga cgattccgca gtattggacg ctatccagtc taaacatttt    2400
actattaccc cctctggcaa aacttctttt gcaaaagcct ctcgctattt tggttttttat    2460 cgtcgtctgg taaacgaggg ttatgatagt gttgctctta ctatgcctcg taattccttt    2520
tggcgttatg tatctgcatt agttgaatgt ggtattccta aatctcaact gatgaatctt    2580
tctacctgta ataatgttgt tccgttagtt cgttttatta acgtagattt tcttcccaa    2640 cgtcctgact ggtataatga gccagttctt aaaatcgcat aaggtaattc acaatgatta    2700
aagttgaaat taaaccatct caagcccaat ttactactcg ttctggtgtt tctcgtcagg    2760
gcaagcctta ttcactgaat gagcagcttt gttacgttga tttgggtaat gaatatccgg    2820
ttcttgtcaa gattactctt gatgaaggtc agccagccta tgcgcctggt ctgtacaccg    2880
ttcatctgtc ctctttcaaa gttggtcagt tcggttccct tatgattgac cgtctgcgcc    2940
tcgttccggc taagtaacat ggagcaggtc gcggatttcg acacaattta tcaggcgatg    3000
atacaaatct ccgttgtact tgtttcgcg cttggtataa tcgctggggg tcaaagatga    3060
gtgttttagt gtattctttc gcctctttcg ttttaggttg gtgccttcgt agtggcatta    3120
cgtattttac ccgtttaatg gaaacttcct catgaaaaag tctttagtcc tcaaagcctc    3180
tgtagccgtt gctaccctcg ttccgatgct gtctttcgct gctgagggtg acgatcccgc    3240
aaaagcggcc tttaactccc tgcaagcctc agcgaccgaa tatatcggtt atgcgtgggc    3300
gatggttgtt gtcattgtcg gcgcaactct cggtatcaag ctgtttaaga aattcacctc    3360
gaaagcaagc tgataaaccg atacaattaa aggctccttt tggagccttt tttttggag    3420 attttcaacg tgaaaaaatt attattcgca attcctttag ttgttccttt ctattctcac    3480
tccgctgaaa ctgttgaaag ttgtttagca aaaccccata cagaaaattc atttactaac    3540
gtctggaaag acgacaaaac tttagatcgt tacgctaact atgagggctg tctgtggaat    3600
gctacaggcg ttgtagtttg tactggtgac gaaactcagt gttacggtac atgggttcct    3660
attgggcttg ctatccctga aaatgagggt ggtggctctg agggtggcgg ttctgagggt    3720
ggcggttctg agggtggcgg tactaaacct cctgagtacg tgatacacc tattccgggc    3780 tatacttata tcaaccctct cgacggcact tatccgcctg gtactgagca aaaccccgct    3840
aatcctaatc cttctcttga ggagtctcag cctcttaata cttcatgtt tcagaataat    3900 aggttccgaa ataggcaggg ggcattaact gtttatacgg gcactgttac tcaaggcact    3960
gaccccgtta aaacttatta ccagtacact cctgtatcat caaaagccat gtatgacgct    4020
tactggaacg gtaaattcag agactgcgct ttccattctg gctttaatga ggatccattc    4080
gtttgtgaat atcaaggcca atcgtctgac ctgcctcaac ctcctgtcaa tgctggcggc    4140
ggctctggtc gtggttctgg tggcggctct gagggtggtg gctctgaggg tggcggttct    4200
```

```
gagggtggcg gctctgaggg aggcggttcc ggtggtggct ctggttccgg tgattttgat    4260
tatgaaaaga tggcaaacgc taataagggg gctatgaccg aaaatgccga tgaaaacgcg    4320
ctacagtctg acgctaaagg caaacttgat tctgtcgcta ctgattacgg tgctgctatc    4380
gatggtttca ttggtgacgt ttccggcctt gctaatggta atggtgctac tggtgatttt    4440
gctggctcta attcccaaat ggctcaagtc ggtgacggtg ataattcacc tttaatgaat    4500
aatttccgtc aatatttacc ttccctccct caatcggttg aatgtcgccc ttttgtcttt    4560
ggcgctggta aaccatatga attttctatt gattgtgaca aaataaactt attccgtggt    4620
gtctttgcgt ttcttttata tgttgccacc tttatgtatg tattttctac gtttgctaac    4680
atactgcgta ataaggagtc ttaatcatgc cagttctttt gggtattccg ttattattgc    4740
gtttcctcgg tttccttctg gtaactttgt tcggctatct gcttactttt cttaaaaagg    4800
gcttcggtaa gatagctatt gctatttcat tgtttcttgc tcttattatt gggcttaact    4860
caattcttgt gggttatctc tctgatatta gcgctcaatt accctctgac tttgttcagg    4920
gtgttcagtt aattctcccg tctaatgcgc ttccctgttt ttatgttatt ctctctgtaa    4980
aggctgctat tttcattttt gacgttaaac aaaaaatcgt ttcttatttg gattgggata    5040
aataatatgg ctgtttattt tgtaactggc aaattaggct ctggaaagac gctcgttacg    5100
gttggtaaga ttcaggataa aattgtagct gggtgcaaaa tagcaactaa tcttgattta    5160
aggcttcaaa acctcccgca agtcgggagg ttcgctaaaa cgcctcgcgt tcttagaata    5220
ccggataagc cttctatatc tgatttgctt gctattgggc gcggtattga ttcctacgat    5280
gaaaataaaa acggcttgct tgttctcgat gagtgcggta cttggtttaa tacccgttct    5340
tggaatgata aggaaagaca gccgattatt gattggtttc tacatgctcg taaattagga    5400
tgggatatta ttttcttgt tcaggactta tctattgttg ataaacaggc gcgttctgca    5460
ttagctgaac atgttgttta ttgtcgtcgt ctggacagaa ttactttacc ttttgtcggt    5520
actttatatt ctcttattac tggctcgaaa atgcctctgc ctaaattaca tgttggcgtt    5580
gttaaatatg gcgattctaa ttaagcccta ctgttgagcg ttggctttat actggtaaga    5640
atttgtataa cgcatatgat actaaacagg ctttttctag taattatgat tccggtgttt    5700
attcttattt aacgccttat ttatcacacg gtcggtattt caaaccatta aatttaggtc    5760
agaagatgaa attaactaaa atatatttga aaaagttttc tcgcgttctt tgtcttgcga    5820
ttggatttgc atcagcattt acatatagtt atataaccca acctaagccg gaggttaaaa    5880
aggtactctc tcagacctat gattttgata aattcactat tgactcttct cagcgtctta    5940
atctaagcta tcgctatcgg ggcaaggatt ctaagggaaa attaattaat agcgacgatt    6000
tacagaagca aggttattca ctcacatata ttgatttatg tactgtttcc attaaaaaag    6060
gtaattcaaa tgaaattgtt aaatgtaatt aattttgttt tcttgatgtt tgtttcatca    6120
tcttcttttg ctcaggtaat tgaaatgaat aattcgcctc tgcgcgattt tgtaacttgg    6180
tattcaaagc aatcaggcga atccgttatt gtttctcccg atgtaaaagg tactgttact    6240
gtatattctt ctgacgttaa acctgaaaat ctacgcaatt tctttatttc tgttttacgt    6300
gcaaataatt ttgatatggt aggttctaac ccttccatta ttcagaagta taatccaaac    6360
aatcaggatt atattgatga attgccatca tctgataatc aggaatatga tgataattcc    6420
gctccttctg gtggtttctt tgttccgcaa aatgataatg ttactcaaac ttttaaaatt    6480
aataacgttc gggcaaagga tttaatacga gttgtcgaat tgtttgtaaa gtctaatact    6540
tctaaatcct caaatgtatt atctattgac ggctctaatc tattagttgt tagtgctcct    6600
```

-continued

```
aaagatattt tagataacct tcctcaattc ctttcaactg ttgatttgcc aactgaccag    6660
atcttgattg agggtttgat atttgaggtt cagcaaggtg atgctttaga ttttcattt     6720 gctgctggct ctcagcgtgg cactgttgca ggcggtgtta atactgaccg cctcacctct    6780
gttttatctt ctgctggtgg ttcgttcggt attttaatg gcgatcgggg agggctctca     6840
gttcgcgcat taaagactaa tagccattca aaatattgt ctgtgccacg tattcttacg     6900 cttttcaggtc agaagggttc tatctctgtt ggccagaatg tcccttttat tactggtcgt   6960
gtgactggtg aatctgccaa tgtaaataat ccatttcaga cgattgagcg tcaaaatgta    7020
ggtatttcca tgagcgtttt tcctgttgca atggctggcg gtaatattgt tctggatatt    7080
accagcaagg ccgatagttt gagttcttct actcaggcaa gtgatgttat tactaatcaa    7140
agaagtattg ctacaacggt taatttgcgt gatggacaga ctcttttact cggtggcctc    7200
actgattata aaaacacttc tcaggattct ggcgtaccgt tcctgtctaa aatcccttta    7260
atcggcctcc tgtttagctc ccgctctgat tctaacgagg aaagcacgtt atacgtgctc    7320
gtcaaagcaa ccatagtacg cgccctgtag cggcgcatta agcgcggcgg tgtggtggt     7380 tacgcgcagc gtgaccgcta cacttgccag cgccctagcg cccgctcctt tcgctttctt    7440
cccttccttt ctcgccacgt tcgccggctt tccccgtcaa gctctaaatc gggggctccc    7500 tttaggggttc cgatttagtg ctttacggca cctcgacccc aaaaaacttg atttgggtga   7560
tggttcacgt agtgggccat cgccctgata gacggttttt cgccctttga cgttggagtc    7620
cacgttcttt aatagtggac tcttgttcca aactggaaca acactcaacc ctatctcggg    7680
acggatcgct tcatgtggca ggagaaaaaa ggctgcaccg gtgcgtcagc agaatatgtg    7740
atacaggata tattccgctt cctcgctcac tgactcgcta cgctcggtcg ttcgactgcg    7800
gcgagcggaa atggcttacg aacggggcgg agatttcctg gaagatgcca ggaagatact    7860
taacagggaa gtgagagggc cgcggcaaag ccgttttcc ataggctccg ccccctgac      7920 aagcatcacg aaatctgacg ctcaaatcag tggtggcgaa acccgacagg actataaaga    7980
taccaggcgt ttccccctgg cggctccctc gtgcgctctc ctgttcctgc ctttcggttt    8040 accgtgtca ttccgctctt atggccgcgt ttgtctcatt ccacgcctga cactcagttc     8100
cgggtaggca gttcgctcca agctggactg tatgcacgaa ccccccgttc agtccgaccg    8160
ctgcgcctta tccggtaact atcgtcttga gtccaacccg gaaagacatg caaaagcacc    8220
actggcagca gccactggta attgatttag aggagttagt cttgaagtca tgcgccggtt    8280
aaggctaaac tgaaaggaca gttttggtg actgcgctcc tccaagccag ttacctcggt     8340
tcaaagagtt ggtagctcag agaaccttcg aaaaaccgcc ctgcaaggcg ttttttcgt     8400 tttcagagca agagattacg cgcagaccaa aacgatctca agaagatcat cttattaagg    8460
ggtctgacgc tcagtggaac gaaaactcac gttaagggat tttggtcatg agattatcaa    8520
aaaggatctt cacctagatc cttttaaatt aaaaatgaag ttttaaatca atctaaagta    8580
tatatgagta aacttggtct gacagttacc aatgcttaat cagtgaggca cctatctcag    8640
cgatctgtct atttcgttca tccatagt                                       8668
```

<210> SEQ ID NO 16
<211> LENGTH: 424
<212> TYPE: PRT
<213> ORGANISM: VCSM13 Helper Phage

<400> SEQUENCE: 16

```
Val Lys Lys Leu Leu Phe Ala Ile Pro Leu Val Val Pro Phe Tyr Ser
1               5                   10                  15
```

His Ser Ala Glu Thr Val Glu Ser Cys Leu Ala Lys Pro His Thr Glu
            20                  25                  30

Asn Ser Phe Thr Asn Val Trp Lys Asp Asp Lys Thr Leu Asp Arg Tyr
            35                  40                  45

Ala Asn Tyr Glu Gly Cys Leu Trp Asn Ala Thr Gly Val Val Val Cys
50                  55                  60

Thr Gly Asp Glu Thr Gln Cys Tyr Gly Thr Trp Val Pro Ile Gly Leu
65                  70                  75                  80

Ala Ile Pro Glu Asn Glu Gly Gly Ser Glu Gly Gly Ser Glu
                85                  90                  95

Gly Gly Gly Ser Glu Gly Gly Thr Lys Pro Pro Glu Tyr Gly Asp
                100                 105                 110

Thr Pro Ile Pro Gly Tyr Thr Tyr Ile Asn Pro Leu Asp Gly Thr Tyr
            115                 120                 125

Pro Pro Gly Thr Glu Gln Asn Pro Ala Asn Pro Asn Pro Ser Leu Glu
            130                 135                 140

Glu Ser Gln Pro Leu Asn Thr Phe Met Phe Gln Asn Asn Arg Phe Arg
145                 150                 155                 160

Asn Arg Gln Gly Ala Leu Thr Val Tyr Thr Gly Thr Val Thr Gln Gly
                165                 170                 175

Thr Asp Pro Val Lys Thr Tyr Tyr Gln Tyr Thr Pro Val Ser Ser Lys
            180                 185                 190

Ala Met Tyr Asp Ala Tyr Trp Asn Gly Lys Phe Arg Asp Cys Ala Phe
            195                 200                 205

His Ser Gly Phe Asn Glu Asp Pro Phe Val Cys Glu Tyr Gln Gly Gln
            210                 215                 220

Ser Ser Asp Leu Pro Gln Pro Val Asn Ala Gly Gly Ser Gly
225                 230                 235                 240

Arg Gly Ser Gly Gly Ser Glu Gly Gly Ser Glu Gly Gly
                245                 250                 255

Ser Glu Gly Gly Gly Ser Glu Gly Gly Ser Gly Gly Ser Gly
            260                 265                 270

Ser Gly Asp Phe Asp Tyr Glu Lys Met Ala Asn Ala Asn Lys Gly Ala
            275                 280                 285

Met Thr Glu Asn Ala Asp Glu Asn Ala Leu Gln Ser Asp Ala Lys Gly
290                 295                 300

Lys Leu Asp Ser Val Ala Thr Asp Tyr Gly Ala Ala Ile Asp Gly Phe
305                 310                 315                 320

Ile Gly Asp Val Ser Gly Leu Ala Asn Gly Asn Gly Ala Thr Gly Asp
                325                 330                 335

Phe Ala Gly Ser Asn Ser Gln Met Ala Gln Val Gly Asp Gly Asp Asn
            340                 345                 350

Ser Pro Leu Met Asn Asn Phe Arg Gln Tyr Leu Pro Ser Leu Pro Gln
            355                 360                 365

Ser Val Glu Cys Arg Pro Phe Val Phe Gly Ala Gly Lys Pro Tyr Glu
370                 375                 380

Phe Ser Ile Asp Cys Asp Lys Ile Asn Leu Phe Arg Gly Val Phe Ala
385                 390                 395                 400

Phe Leu Leu Tyr Val Ala Thr Phe Met Tyr Val Phe Ser Thr Phe Ala
                405                 410                 415

Asn Ile Leu Arg Asn Lys Glu Ser
                420

<210> SEQ ID NO 17
<211> LENGTH: 266
<212> TYPE: DNA
<213> ORGANISM: VCSM13 Helper Phage

<400> SEQUENCE: 17

```
ggttatgcgt gggcgatggt tgttgtcatt gtcggcgcaa ctatcggtat caagctgttt      60
aagaaattca cctcgaaagc aagctgataa accgatacaa ttaaaggctc cttttggagc     120
cttttttttt ggagattttc aacaagcttc tgcgtaataa ggagtcttaa tcatgccagt     180
tcttttgggt attccgttat tattgcgttt cctcggtttc cttctggtaa ctttgttcgg     240
ctatctgcta acttttctta aaaagg                                         266
```

<210> SEQ ID NO 18
<211> LENGTH: 832
<212> TYPE: DNA
<213> ORGANISM: VCSM13 Helper Phage

<400> SEQUENCE: 18

```
ttgactccct gcaagcctca gcgaccgaat atatcggtta tgcgtgggcg atggttgttg      60
tcattgtcgg cgcaactatc ggtatcaagc tgtttaagaa attcacctcg aaagcaagct     120
gataaaccga tacaattaaa ggctcctttt ggagcctttt ttttggcga ttttcaacgt     180 gaaaaaatta ttattcgcaa ttcctttagt tgttcctttc tattctcact ccgctggatc     240
ctctggttcc ggtgattttg attatgaaaa tatggcaaac gctaataagg gggctatgac     300
cgaaaatgcc gatgaaaacg cgctacagtc tgacgctaaa gcaaacttg attctgtcgc     360 tactgattac ggtgctgcta tcgacggttt cattggtgac gtttccggcc ttgctaatgg     420
taatggtgct actggtgatt ttgctggctc taattcccaa atggctcaag tcggtgacgg     480
tgataattca ccttttattga ataatttccg tcaatattta ccttcccttc ctcaatcggt     540
tgaatgtcgc ccttttgtct ttcgcgctgg taaaccatat gaattttcta ttgattgtga     600
caaaataaac ttattccgtg gtgtctttgc gtttctttta tatgttgcca cctttatgta     660
tgtattttcg acgtttgcta acatactgcg taataaggag tcttaatcat gccagttctt     720
ttgggtattc cgttattatt gcgtttcctc ggtttccttc tggtaacttt gttcggctat     780
ctgctaactt tcttaaaaaa gggcttcggt aagatagcta ttgctattc at             832
```

<210> SEQ ID NO 19
<211> LENGTH: 12
<212> TYPE: DNA
<213> ORGANISM: Unknown
<220> FEATURE:
<223> OTHER INFORMATION: codon used to generate non-homologous g3 gene

<400> SEQUENCE: 19

```
gcggcagccg ct                                                          12
```

CHIMAERIC PHAGES

CROSS REFERENCE TO RELATED APPLICATIONS

This application is divisional of application Ser. No. 10/480,978, filed Sep. 2, 2004, now U.S. Pat. No. 7,329,530 B2 issued Feb. 12, 2008, which is a national stage entry of and claims priority under 35 U.S.C. §365 to PCT/NL02/00391, filed Jun. 14, 2002, designating the United States of America, corresponding to PCT International Publication WO 02/103012 (published in English on Dec. 27, 2002), the contents of which are incorporated herein in their entireties. PCT NL02/00391 itself claims priority to both European Patent Office 01202304.0 filed on Jun. 15, 2001 and U.S. Ser. No. 09/882,621 (now U.S. Pat. No. 7,070,926, Jul. 4, 2006), both of which were filed on Jun. 15, 2001.

TECHNICAL FIELD

The present invention relates generally to biotechnology and more particularly to the fields of molecular biology and immunology. The invention in particular relates to the field of generating helper phages and phage display libraries for the identification of binding molecules.

BACKGROUND

An individual needs to have a dynamic immune system that is able to adapt rapidly and respond adequately to potentially harmful microorganisms, and to respond to the exposure of a highly diverse and continuously changing environment. Higher organisms have evolved specialized molecular mechanisms to ensure the implementation of clonally-distributed, highly diverse repertoires of antigen-receptor molecules expressed by cells of the immune system: immunoglobulin (Ig) molecules on B lymphocytes and T cell receptors on T lymphocytes. A primary repertoire of (generally low affinity) Ig receptors is established during B cell differentiation in the bone marrow as a result of rearrangement of germ line-encoded gene segments. Further refinement of Ig receptor specificity and affinity occurs in peripheral lymphoid organs where antigen-stimulated B lymphocytes activate a somatic hypermutation machinery that specifically targets the immunoglobulin variable (V) regions. During this process, B cell clones with mutant Ig receptors of higher affinity for the inciting antigen are stimulated into clonal proliferation and maturation into antibody-secreting plasma cells (reviewed in Berek and Milstein. 1987).

Recombinant DNA technology has been used to mimic many aspects of the processes that govern the generation and selection of natural human antibody repertoires (reviewed in Winter and Milstein. 1991; Vaughan et al. 1998). The construction of large repertoires of antibody fragments (such as Fab fragments or single chain Fv fragments, scFv's) expressed on the surface of filamentous phage particles and the selection of such phages by "panning" on antigens has been developed as a versatile and rapid method to obtain antibodies of desired specificities (reviewed in Burton and Barbas. 1994). A subsequent optimization of the affinity of individual phage antibodies was achieved by creating mutant antibody repertoires of the selected phages and sampled for higher affinity descendents by selection for binding to antigen under more stringent conditions (reviewed in Hoogenboom. 1994).

M13 and M13-derived phages (sometimes also called viruses) are filamentous phages that can selectively infect F-pili bearing (F$^+$) *Escherichia coli* (*E. coli*) cells. The phage genome encodes 11 proteins, while the phage coat itself consists of 5 of these proteins: gene3, -6, -7, -8 and -9 (g3, g6, g7, g8 and g9) proteins that are bound to and that protect the (circular) single stranded DNA (ssDNA) of the viral genome. The life cycle of the virus can be subdivided into different phases.

The g3 protein (g3p) of M13 phages and M13-derivatives comprises three functional domains: D1, D2 and D3, linked by two glycine-rich linkers. An alternative nomenclature for g3p domains has also been generally accepted, in which D1, D2 and D3 are named "N1," "N2" and "CT," respectively. The N-terminal D1/D2 regions interact with the C-terminal D3 region as has been found by Chatellier et al. (1999) using several deletion mutants of g3p. Considering that functionality of a D3 domain of the protein is required for assembly of stable phages, a less-, or non-infectious mutant of the phage coat protein preferably comprises a D3 region of the g3p, or comprises a functional part, derivative and/or analogue of the D3 region. The D3 domain is thought to bind to DNA inside the viral particle. Loss of the D3 domain functionally results in rare phage-like particles that are very long and very fragile (Pratt et al. 1969; Crissman and Smith. 1984; Rakonjac and Model. 1998). The D1 and D2 domain are thought to interact with each other until the phage binds to the bacteria, while D1/D2 also interact with D3 at certain stages (Chatellier et al. 1999). The linkers present in g3p between D1, D2 and D3 apparently also play a role in infectivity of the phage particle (Nilsson et al. 2000).

Studies in which a protease cleavage site was introduced between D1 and D2 showed that after cleavage, the phage particle became non-infectious (Kristensen and Winter. 1998). Functional analysis of g3p showed that of the g3p N-terminal regions, the D1 domain is essential for infection. Loss of this domain results in phages that cannot infect bacteria (Lubkowski et al. 1998; Nelson et al. 1981; Deng et al. 1999; Riechmann and Holliger. 1997; Holliger and Riechmann. 1997). It has been shown that the D2 domain interacts with the D1 domain of g3p on the phage (FIG. 1). Due to competition of proteins located on the F-pilus (on F+bacteria) that have higher affinity for D2 than for D1, the D1 and D2 domain of the g3p dissociate from each other.

The binding of D2 to the F-pilus results in a process that leads to retraction of the F-pilus towards the *E. coli* cell membrane. Due to this process, the phage particle comes in close contact with the bacterial membrane. The dissociated D1 domain can interact with bacterial proteins such as the TolA receptor, leading to the introduction of the phage DNA into the *E. coli* cell (Lubkowski et al. 1999). The fact that removal of the D2 domain does not prevent infection, but enables phages to infect *E. coli* lacking F-pili (Riechmann and Holliger. 1997; Deng et al. 1999) shows that the presence of the D2 domain increases specificity and that D2 has an important role in preventing F-pili independent infections. The binding of D1 to the specific receptors on the surface of the *E. coli* cell (a feature that is not F$^+$-specific) is represented in FIG. 2. This process triggers the injection of the viral genome into the bacterium (as depicted in FIG. 3).

Although loss of the D2 domain results in the formation of phage particles that can infect *E. coli* in a somewhat reduced specific manner, it appears that the level of infections from such a population of phages is significantly reduced. After infection of an *E. coli* by a phage particle, the ssDNA of the virus becomes double stranded due to the action of a number of bacterial enzymes. The double stranded phage genome serves as a template for the transcription and translation of all 11 genes located on the phage genome. Besides these protein-encoding regions, the phage genome contains an intergenic region: the F1-origin of replication initiation (F1-ORI). The DNA sequence of this F1-ORI can be divided in 2 separate subregions. One subregion is responsible for the initiation and termination of the synthesis of ssDNA via the so-called 'rolling circle mechanism' and the other subregion is responsible for the packaging initiation of the formed circular ssDNA leading to the formation and release of new virus particles.

It has been shown that polypeptides, such as stretches of amino acids, protein parts or even entire proteins can be added by means of molecular genetics to the terminal ends of a number of particle coat proteins, without disturbing the functionality of these proteins in the phage life cycle (Smith. 1985; Cwirla et al. 1990; Devlin et al. 1990; Bass et al. 1990; Felici et al. 1993; Luzzago et al. 1993).

This feature enables investigators to display peptides or proteins on phages, resulting in the generation of peptide- or protein expression phage display libraries. One of the proteins that has been used to fuse with polypeptides for phage display purposes, is the g3 protein (g3p), which is a coat protein that is required for an efficient and effective infectivity and subsequent entry of the viral genome into the *E. coli* cell.

For the production of phages that display polypeptides fused to the g3p coat protein, investigators introduced a plasmid together with the phage genome in *E. coli* cells. This plasmid contains an active promoter upstream of an in-frame fusion between the g3 encoding gene and a gene of interest (X) encoding, for instance, polypeptides such as proteins such as antibodies or fragments such as Fab fragments or scFv's. The introduction of this plasmid together with the genome of the helper phage in an *E. coli* cell results in the generation of phages that contain on their coat either the wild type g3p from the viral genome, the fusion product g3p-X from the plasmid or a mixture of the two, since one phage particle carries five g3p's on its surface. The process of g3p or g3p-X incorporation is generally random.

The presence of an F1-ORI sequence in the g3p-X expression vector (plasmid) misleads the phage synthesis machinery in such a way that two types of circular ssDNA are formed: one is derived from the genome of the phage and the other is derived from the expression vector. During the synthesis of new phages, the machinery is unable to distinguish the difference between these two forms of ssDNA resulting in the synthesis of a mixed population of phages, one part containing the phage genome and one part harboring the vector DNA. Due to these processes, the mixture contains at least some phages in which the phenotypic information on the outside (the g3p-X fusion protein) is conserved within the genotypic information inside the particle (the g3p-X expression vector). An infectious wild type phage and a phage carrying a fusion protein attached to g3p are depicted in FIG. 4. The art teaches that there are several problems that concern the use of these basic set-ups.

The high level of genotypic wild type phages in phage populations grown in bacteria that contain both the phage genome and the expression vector compelled investigators to design mutant F1-ORI sequences in M13 genomes. Such mutant M13-strains are less effective in incorporating their genome in phage particles during phage assembly, resulting in an increased percentage of phages containing vector sequences when co-expressed. These mutant phages, such as the commercially available strains R408, VCSM13 and M13KO7, are called "helper phages." The genome of these helper phages may contain genes required to assemble new (helper-) phages in *E. coli* and to subsequently infect new F-pili expressing *E. coli*. Both VCSM13 and M13K07 were provided with an origin of replication initiation (ORI) of the P15A type that results in the multiplication of the viral genome in *E. coli*. Moreover, the ORI introduction ensures that after cell division the old and newly formed *E. coli* contains at least one copy of the viral genome.

It was suggested and finally proven by several investigators that the introduction of plasmids containing a g3p-scFv fusion product together with the genome of the helper phages in *E. coli* cells results in approximately 99% of newly formed phages that harbor the g3p-scFv fusion protein expression plasmid, but nevertheless lack the g3p-scFv fusion on its surface (Beekwilder et al. 1999). The absence of g3p-X is a significant disadvantage in the use of display libraries for the identification of specific proteins or peptides such as scFv's that bind to a target of interest (such as tumor antigens). It implies that in the case of phage display libraries, at least a 100-fold excess of produced phages must be used in an experiment in order to perform a selection with all possible fusion proteins present.

The art teaches that this overload of relatively useless phages in an experiment leads to (too) many false positives. For instance, at least $10^{12}$ phages should be added to a panning experiment in order to have 1 copy of each possible fusion present in the experiment, since such a library contains approximately $10^{10}$ different g3p-scFv fusions (1%). The phages in this approximate 1% express generally only 1 g3p-scFv fusion on their coat together with four normal g3p's (no fusions), while the rest of the helper phages (approximately 99%) express five g3p's and no g3p-scFv fusions. To ensure, theoretically, the presence of 100 copies of each separate fusion protein in a panning experiment, one needs to use approximately $10^{14}$ phages in such an experiment. Persons skilled in the art generally attempt to use an excess of at least 100-fold of each single unique fusion protein, to ensure the presence of sufficient numbers of each separate fusion and not to lose relevant binders too quickly in first panning rounds. That number of phages ($10^{14}$) is more or less the maximum of phage particles that a milliliter (ml) can hold. The viscosity of such a solution is extremely high and therefore relatively useless. Especially when ELISA panning strategies are used (in which the volume of one well is only 200 µl) such libraries cannot be used.

In addition to these problems, it is assumed that, generally, depending on the antigen and the stringency of washing procedures, an average of 1 in every 1 phages will bind to the antigen due to a-specific binding. Thus, for the application of $10^{12}$ scFv expressing input phages (1%) to a panning procedure, one has to add approximately $10^{14}$ phages (99% of which do not express a scFv fragment). It is generally assumed that from these $10^{12}$ phages, approximately $10^4$ particles might be putatively interesting phages. However, depending on the washing conditions, the number of calculated background phages that are normally found by using libraries present in the art after one round of panning, was approximately $10^6$-$10^7$ while only a few of these phages appear to be relevant binders. This is one of the most significant problems recognized in the art: too many background phages show up as initial binders in the phage mix after the first round of panning, while only a few significant and interesting binders are present in this mix. Thus, the absolute number of isolated phages after one round of panning is clearly too high ($10^6$-$10^7$). Moreover, in subsequent rounds of panning, non-specific background phages remain present. In libraries used in the art, most of these non-specific binders will amplify on bacteria that, upon amplification, continue to in a second round of panning. Therefore, the art teaches that the background level of a-specifically binding phages and the total number of phages per ml in these types of libraries is unacceptably high and remains high during subsequent rounds of panning.

A possibility that was suggested by investigators in the art as a solution to the problem of obtaining too many background phages that lack a g3p-X fusion was to remove the g3p-encoding gene entirely from the helper phage genome. In principle, this system ensures that during phage synthesis in an *E. coli* cell (that received the g3-less phage genome and a g3p-X fusion protein expression vector), only g3p-X proteins are incorporated in the newly formed phage coat. By doing so, each synthesized phage will express five copies of the g3p-X fusion product and hardly any phages are synthesized that express the g3p alone or that express less than five g3p-X fusions. R408-d3 and M13MDΔD3 are two examples of g3-minus helper phages (Dueñas and Borrebaeck. 1995; Rakonjac et al. 1997). Because the genome of these phages is not capable of supporting g3p synthesis, phage particles that carry less than five g3p-X fusion proteins can hardly be formed, or, if formed, are found to be non-infectious due to instability, since the art teaches that five g3p's are necessary to ensure a stable phage particle.

To produce helper phages that do not contain the g3 gene, but that are nevertheless infectious and that can be used to generate libraries of phages that carry five g3p-X fusion proteins, and that lack phages with less than five g3p-X fusions, it was recognized in the art that an external source for g3p was required. Such a source can be a vector without F1-ORI but that nevertheless contains an active promoter upstream of the full open reading frame (ORF) of g3. One major problem that is recognized by persons skilled in the art is that after the generation step of producing newly formed helper phages lacking a g3 gene, the yield is dramatically low. In fact, the yield of all described systems is below $10^{10}$ phages per liter, meaning that for a library of $10^{10}$ individual clones, at least 100 liters of helper phage culture are necessary (NB: the helper phages need to be purified) in order to grow the library once. The art, thus, teaches that phage libraries generated with such low titers of helper phages are not useful for phage display purposes and that these libraries cannot be used for panning experiments. One method for complementation of g3p deletion phages was presented recently, in which wild-type g3p was provided by a nucleic acid encoding the wild-type g3p, wherein the nucleic acid was stably incorporated into the host cell genome (Rondot et al. 2001).

Phages that express deleted g3p's fused to heterologous proteins have been generated. For the construction of most conventional Fab libraries and some scFv phage display libraries, the D1 domain and parts of the D2 domain were removed to ensure a shorter fusion protein, which was considered in the art as a product that could be translated easier than a full length g3p linked to a full length Fab fragment. The shorter g3p part would not prevent the generation of a viable and useful helper phage. Of course, such phages still depend on full length g3p's that are present on their surface next to the deleted g3p fusion with the Fab fragment for functional infectivity of *E. coli* cells. Also, phages that express deleted g3p's fused to ligand-binding proteins have been generated that depend on their infectious abilities on antigens that were fused to the parts of g3p that were missing from the non-infectious phage particle (Krebber et al. 1997; Spada et al. 1997). These particles depend for their infectivity on an interaction between the ligand-binding protein, such as an antibody or a fragment thereof and their respective ligand (or antigen). However, this interaction-dependency reduces the efficiency of infection, due to elimination of a direct linkage between the g3p domains, and a general inhibitory effect of the soluble N-terminal part of g3p coupled to the antigen.

The g3-minus helper phages R408-d3 and M13MDΔD3 mentioned above lack a bacterial ORI and a selection marker in their genome. The absence of a selection marker in the g3-minus genomes has a significant effect on the production scale of helper phages, because it results in an overgrowth of bacteria that do not contain the helper phage genome. It is known that bacteria grow slower when infected with the helper phage or virus. Therefore, bacteria that lack the phage genome quickly overgrow the other bacteria that do contain the genome. Another effect of the lack of an ORI or a selection marker is that g3-minus phage genomes cannot be kept in dividing bacteria during the production and expansion of phage display libraries. This is a very important negative feature because overgrowth of bacteria that lost the phage genome or that never received one, appear to have a growth advantage over bacteria that do contain the phage genome. In addition, such 'empty' bacteria are not capable of producing any phage and as a result, the phage display vectors including fusion protein fragments in such helper phages lacking-bacteria are lost permanently.

As mentioned, the g3p's are thought to be essential for the assembly of stable M13-like phages and because of their crucial role in infection, g3p's should be provided otherwise when g3-minus helper phages are to be generated. There is a prejudice in the art against making phage display libraries that lack g3p's because phages lacking g3p's are not stable. Rakonjac et al. (1997) constructed a VCSM13 g3-minus helper phage in parallel to a R408 g3-minus helper phage and used helper plasmids with either the psp or the lac promoter upstream of a full length g3 sequence to substitute g3 during helper phage synthesis (Model et al. 1997). However, the art teaches that the lac promoter has the disadvantage that it cannot be shut off completely, even not in the presence of high concentrations of glucose (3-5%) in the medium (Rakonjac and Model. 1998).

An additional problem that is well known in the art is that even very low levels of g3p in *E. coli* can block infection of M13-like phages. Moreover, it has been shown that co-encapsidation of plasmids together with the phage genome can occur (Russel and Model. 1989; Krebber et al. 1995; Rakonjac et al. 1997). If co-encapsidation occurs with the lac driven helper plasmid, it will compete with the lac driven vectors used in the phage display resulting in the efficient production of infectious phage particles that will not contain the g3p-X fusion product. Together, the art thus teaches that the lac promoter is not the best candidate promoter in the helper plasmid system. The psp promoter has the advantage to be relatively silent in *E. coli* until infection (Rakonjac et al. 1997). Upon M13-class phage infection, the psp promoter becomes activated and the helper plasmid will produce g3 proteins. However, the disadvantage of this promoter is that the level of RNA production cannot be regulated with external factors, but has to be regulated by either mutating (and change the activity of) the promotor, changing the ribosomal binding site (RBS) or other elements that influence the promotor activity. To figure out the ideal level of promotor activity in a specific *E. coli* strain can be time consuming and needs to be optimized for each *E. coli* strain separately. The art also teaches that the psp promotor system is not very attractive for large-scale helper phage production due to the inflexibility of *E. coli* strains, the time consuming optimization and the significant low level of helper phage production.

A significant problematic feature helper phage systems described is the occurrence of unwanted recombination events between the helper genome and the (helper-) plasmids.

The problem that confronts investigators in the art is the fact that the g3 DNA sequences in the helper phages are homologous to the g3 sequences in the phage display vector and/or the helper phage plasmid. This results, in many cases, in recombination between the two DNA strains and therefore loss of functionality of the library as a whole.

SUMMARY OF THE INVENTION

The current invention provides chimaeric phages, novel helper phages, libraries comprising the chimaeric phages and methods and means to produce the chimaeric phages and the helper phages.

In one embodiment, the invention provides a chimaeric phage having a coat comprising a mixture of proteins, the mixture comprising a fusion protein, wherein a proteinaceous molecule is fused to a functional form of a phage coat protein. The mixture further comprises a mutant form of the phage coat protein, the mutant form being impaired in binding to a host cell receptor. The invention also provides a chimaeric phage having a coat comprising a mixture of proteins, the mixture comprising a fusion protein, wherein a proteinaceous molecule is fused to a phage coat protein, or to a fragment or derivative thereof. The fusion protein is functional so as to render the chimaeric phage infectious, the mixture further comprises a mutant form of the phage coat protein, the mutant form being impaired in binding to a host cell receptor.

In another embodiment, the invention provides a helper phage comprising a nucleic acid encoding phage proteins or functional equivalents thereof that are essential for the assembly of the helper phage. The nucleic acid further encodes a mutant form of a phage coat protein, the mutant form being impaired in binding to a host cell receptor, and wherein the helper phage does not comprise nucleic acid encoding a functional form of the phage coat protein.

In yet another embodiment, the invention further provides methods and means for producing phage particles, chimaeric phages, infectious phages and helper phages. The invention also provides phage collections, such as phage display libraries comprising chimaeric phages and/or infectious phages.

BRIEF DESCRIPTION OF THE DRAWINGS

FIGS. 6A-6D. (FIG. 6A) Schematic representation of the VCSM13 helper phage genome. The 11 genes are indicated, as well as the kanamycin resistance gene (Kan R), the packaging signal (PS) and the large and small fragments of the original intergenic region (IG). (FIG. 6B) Sequence of the VCSM13 genome (SEQ ID NO: 15) shown in FIG. 6A. The translation of the g3 gene (SEQ ID NO: 16) is given in one letter code. (FIG. 6C) Schematic representation of the VCSM13-derived g3-minus helper phage genome deleted for the open reading frame (ORF) of the g3 gene. (FIG. 6D) Sequence (SEQ ID NO: 17) of the part of the helper phage genome that surrounds the position of the g3 deletion depicted in FIG. 6C. The HindIII site at position 3431 is underlined, followed by the 6 codons in bold face upstream of the TAA stop codon.

FIGS. 7A-7b. (FIG. 7A) Schematic representation of the VCSM13-derived D3 helper phage genome deleted for the D1 and D2 domains of the g3 gene. The D3 part of the g3 gene encodes the carboxy-terminal part of the g3 protein enabling the generation of stable, but essentially non-infectious helper phages. The D3 helper phage genome is identical to the CT helper phage genome. (FIG. 7B) Sequence (SEQ ID NO: 18) of the sequence listing incorporated herein of the D3 domain of g3 present in the nucleic acid shown in FIG. 7A. The BamHI site at position 3488 as well as the GTG start en TAA stop codon are underlined.

FIG. 8. Codon usage adaptation in the g3 gene and the D3 domain to prevent homologous recombination during helper phage production and during phage display library amplification. The left panel shows the obtained one-letter coded amino acids and the right panel shows the optimal codons.

DETAILED DESCRIPTION

Figure 1:
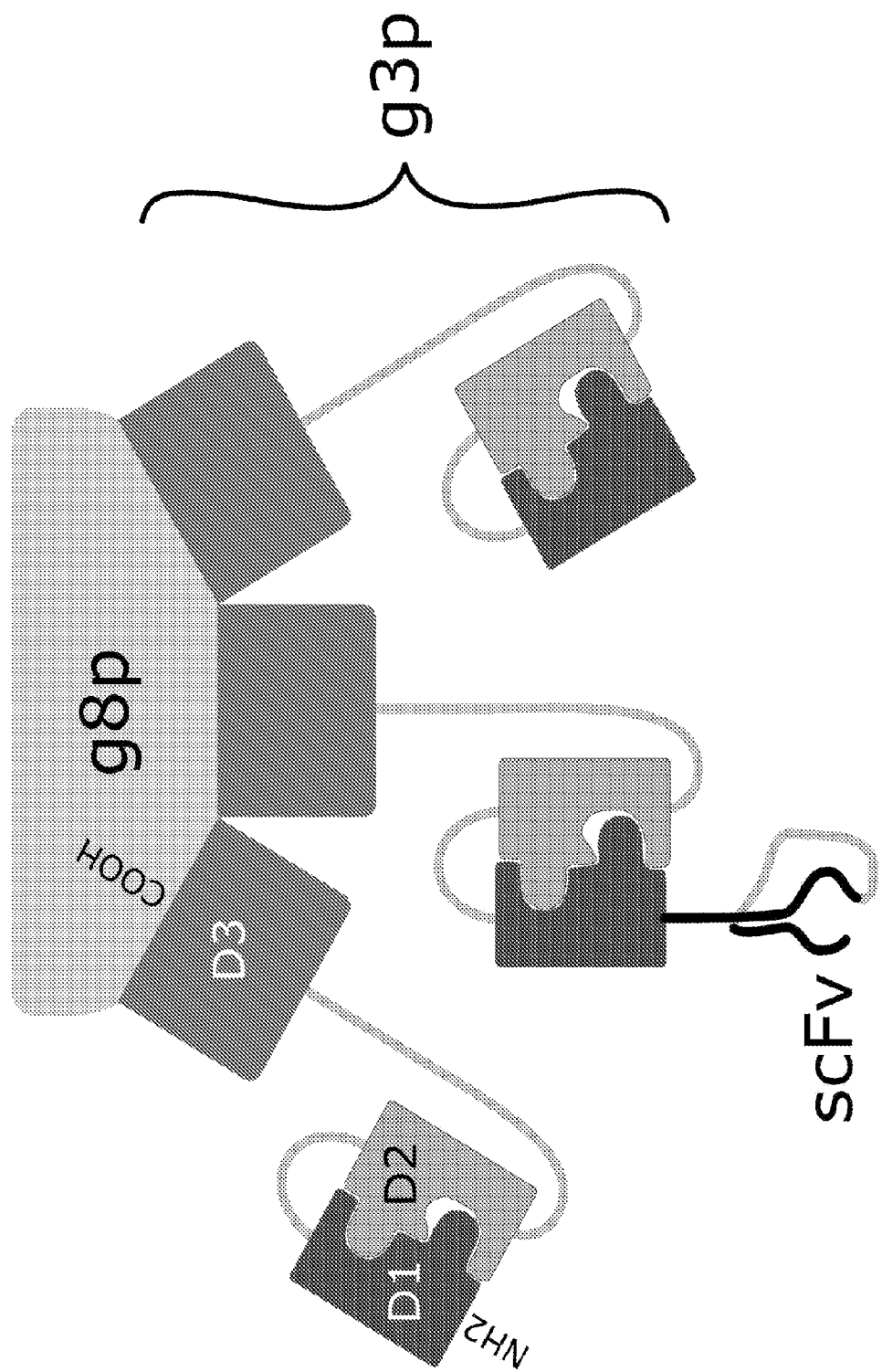
FIG. 1. Schematic representation of the g3 protein (g3p) present in the coat of M13 phages. The D3 domain of g3p is attached to the single stranded DNA inside the particle via the g8 protein (g8p), while the D1 and D2 domains interact with each other outside the particle and can be used for fusion with for example scFv.

The present invention provides a chimaeric phage having a coat comprising a mixture of proteins, the mixture comprising a fusion protein, wherein a proteinaceous molecule is fused to a functional form of a phage coat protein. The mixture further comprises a mutant form of the phage coat protein, wherein the mutant form is characterized in that a phage comprising no wild type phage coat protein from which the mutant form is derived and having a coat comprising the mutant form and no copies of the functional form, is less infectious than a phage comprising no wild type phage coat protein from which the mutant form is derived and having a coat comprising the mutant form and at least one copy of the functional form.

In one embodiment of the invention, the mutant form is characterized in that a phage comprising no wild type phage coat protein from which the mutant form is derived and carrying the mutant form and no copies of the fusion protein is less infectious than a phage comprising no wild type phage coat protein from which the mutant form is derived and carrying in addition to the mutant form, at least one copy of the fusion protein.

Preferably, the mutant form is characterized in that a phage comprising no wild type phage coat protein from which the mutant form is derived and carrying the mutant form and no copies of the fusion protein or the functional form is noninfectious. More preferably, the mutant form is further characterized in that a phage having a coat comprising the mutant form in the presence or absence of copies of the functional form, is stable. Stable as used herein means that the part of g3p that is still present in the mutant form (and that is also present in the functional form) ensures features such as DNA binding and rigidity of the phage, but does not contribute to infectiousness of the phage as do the domains in the functional form that are not present in the mutant form.

The invention also provides an infectious phage containing at least one copy of a mutant form of a phage coat protein, wherein the mutant form has lost the ability to mediate infection of a natural host by the infectious phage.

In a preferred embodiment, the phage coat protein is the g3 protein (g3p) present in the coat of phages such as M13 and R408. More preferably, the mutant form comprises a mutation in the D1 and/or the D2 region of g3p.

In another preferred aspect of the invention, the chimaeric phage and/or the infectious phage are part of a phage collection such as a phage display library. In a more preferred aspect of the invention, such a phage collection consists essentially of chimaeric phages or infectious phages provided by the invention. Also preferred are chimaeric phages or infectious phages according to the invention that comprise binding moieties, such as antibodies or fragments thereof as part of the fusion protein.

In another embodiment, the invention provides a method for producing a phage particle comprising the steps of: providing a host cell with a first nucleic acid encoding a fusion protein, the fusion protein comprising a proteinaceous molecule fused to a functional form of a phage coat protein; providing the host cell with a second nucleic acid encoding a mutant form of the phage coat protein, the mutant form being characterized in that a phage comprising no wild type phage coat protein from which the mutant form is derived and having a coat comprising the mutant form and no copies of the functional form is less infectious than a phage comprising no wild type phage coat protein from which the mutant form is derived and having a coat comprising at least one copy of the functional form. The host cell further comprises an additional nucleic acid sequence encoding at least all other proteins or functional equivalents thereof that are essential for the assembly of the phage particle in the host cell. and the method further comprises culturing the host cell to allow assembly of the phage particle.

The invention provides a method for producing a phage particle, the method comprising the steps of: providing a host cell with a first nucleic acid encoding a fusion protein, the fusion protein comprising a proteinaceous molecule fused to a functional form of a phage coat protein; providing the host cell with a second nucleic acid encoding a mutant form of the phage coat protein, the mutant form being impaired in binding to a host cell receptor; and culturing the host cell to allow assembly of the phage particle.

Preferably, these methods according to the invention for producing a phage particle are applied for producing the chimaeric phage and/or the infectious phage. More preferably, the method is applied for producing a phage particle such as a chimaeric phage or an infectious phage provided by the invention that comprise nucleic acid encoding the mutant form under the control of a controllable promoter such as the AraC/BAD promoter, the lac promoter or the psp promoter.

In another embodiment, the invention provides a helper phage comprising nucleic acid encoding phage proteins or functional equivalents thereof that are essential for the assembly of the helper phage. The nucleic acid further encodes a mutant form of a phage coat protein, wherein the mutant form is characterized in that a phage comprising no wild type phage coat protein from which the mutant form is derived and having a coat comprising the mutant form and no copies of a functional form of the phage coat protein, is less infectious than a phage comprising no wild type phage coat protein from which the mutant form is derived and has a coat comprising at least one copy of the functional form, wherein the functional form is characterized in that it renders a phage particle carrying the functional form in its coat infectious, and wherein the helper phage does not comprise expressible nucleic acid encoding the functional form. The invention provides a helper phage comprising nucleic acid encoding phage proteins or functional equivalents thereof that are essential for the assembly of the helper phage, the nucleic acid further encodes a mutant form of a phage coat protein, the mutant form being impaired in binding to a host cell receptor, and wherein the helper phage does not comprise nucleic acid encoding a functional form of the phage coat protein.

In yet another embodiment, the invention provides a method for producing a helper phage comprising the steps of: providing a host cell with a first nucleic acid encoding a functional form of a phage coat protein; providing the host cell with a second nucleic acid encoding a mutant form of the phage coat protein, wherein the mutant form is characterized in that a phage comprising no wild type phage coat protein from which the mutant form is derived. The helper phage has a coat comprising the mutant form and is less infectious than a phage comprising no wild type phage coat protein from which the mutant form is derived and has a coat comprising at least one copy of the functional form. The host cell comprises an additional nucleic acid sequence encoding at least all other proteins or functional equivalents thereof that are essential for the assembly of the helper phage in the host cell. The method further includes culturing the host cell to allow assembly of the helper phage.

The invention also provides a method for producing a helper phage comprising the steps of: providing a host cell with a first nucleic acid encoding a functional form of a phage coat protein; providing the host cell with a second nucleic acid encoding a mutant form of a phage coat protein, the mutant form being impaired in binding to a host cell receptor. The host cell comprises an additional nucleic acid sequence encoding at least all other proteins or functional equivalents thereof that are essential for the assembly of the helper phage in the host cell. The method further includes culturing the host cell to allow assembly of the helper phage.

In another aspect, the invention provides methods and means for producing a phage particle such as a chimaeric phage, an infectious phage or a helper phage according to the invention, wherein separate nucleic acids encoding either (1) a functional form of the phage coat protein alone or fused to a proteinaceous molecule or (2) a mutant form of the phage coat protein. The chimaeric phage, the infections phage or the helper phage each comprise codons in the overlapping regions between the protein encoding parts, that essentially do not render a homologous recombination event between the separate nucleic acids. In a preferred aspect the separate nucleic acids each comprise non-interfering origins of replication and unique selection markers.

In another embodiment, the invention provides a method for the enrichment of a first binding pair member in a repertoire of first binding pair members selected from the group consisting of: an antibody, an antibody fragment, a single chain Fv fragment, a Fab fragment, a variable region, a CDR region, an immunoglobulin or a functional part thereof. The first binding pair member is specific for a second binding pair member. The method comprises the steps of: contacting a phage collection comprising chimaeric or infectious phages according to the invention with material comprising the second binding pair member under conditions allowing specific binding; removing non-specific binders; and recovering specific binders. The specific binders comprise the first binding pair member. The material may comprise second binding pair members such as purified proteins, recombinant proteins and/or proteins present in or on cells.

In a preferred embodiment, the invention provides a method for the enrichment of a first binding pair member that comprises the steps of: recovering from a phage a DNA sequence encoding the first specific binding pair member; sub-cloning the DNA sequence in a suitable expression vector; expressing the DNA sequence in a suitable host; and culturing the suitable host under conditions whereby the first specific binding pair member is produced. A suitable expression vector may be a plasmid vector comprising an active promoter that regulates the expression of the first specific binding pair member in suitable hosts including eukaryotic cells, such as, yeast cells or mammalian cells.

In another aspect, the invention provides a nucleic acid molecule comprising a sequence encoding a mutant form of a phage coat protein. The mutant form is characterized in that a phage, comprising no wild type phage coat protein from which the mutant form is derived and having a coat comprising the mutant form and no functional form of the phage coat protein, is less infectious than a phage comprising no wild type phage coat protein from which the mutant form is derived and having a coat comprising the mutant form and at least one copy of the functional form of the phage coat protein. The functional form is characterized in that it renders a phage carrying the functional form in its coat infectious. The nucleic acid molecule may furthermore comprise all relevant nucleic acid encoding proteins that are required for assembly of a phage in a host cell.

The invention provides a chimaeric phage having a coat comprising a mixture of proteins, the mixture comprising a fusion protein, wherein a proteinaceous molecule is fused to a functional form of a phage coat protein. The mixture further comprises a mutant form of the phage coat protein, wherein the mutant form is characterized in that a phage comprising no wild type phage coat protein from which the mutant form is derived and having a coat comprising a mutant form of the phage coat protein and no copy or copies of the functional form of the phage coat protein, is less infectious than a phage comprising no wild type phage coat protein from which the mutant form is derived and having a coat comprising at least one functional form of the phage coat protein.

"Functional form" as used herein refers to a phage coat protein that contributes significantly to the infectiousness of the particle to which it is attached. The phage coat protein itself is not infectious, but the functional form renders the phage particle to which it is attached infectious. Besides the contribution to infectivity of the phage particle, the phage coat protein also sustains other functions, such as stabilization of the phage particle.

A "mutant form" of a phage coat protein according to the invention may render the phage particle less infectious or non-infectious, but should still sustain other functions of the phage coat protein such as stabilization of the phage. A phage that comprises no wild type phage coat protein from which the mutant form is derived or originates and comprises no functional forms of the phage coat protein, but does contain only mutant forms of the phage coat protein is less infectious than a phage that comprises no wild type phage coat protein from which the mutant form is derived and comprises one or more functional forms of the phage coat protein next to the mutant forms of the phage coat protein in its coat. "Less infectious" as used herein may also mean non-infectious.

Although a chimaeric phage of the invention comprises at least one copy of the mutant form of the phage coat protein in its coat, the chimaeric phage has infectious capability because it also comprises at least one functional form of the phage coat protein in its coat.

A "functional form of a phage coat protein" as used herein also means a part, derivative and/or an analogue thereof that still harbors functionality in rendering the phage infectious to which it is attached.

"Mutant form of a phage coat protein" as used herein also means a part, a derivative and/or an analogue of the mutant form, wherein the mutant form is characterized in that a phage, comprising no wild type phage coat protein from which the mutant form is derived and having a coat comprising only mutant forms of the phage coat protein or parts, derivatives and/or analogues thereof, is less- or non-infectious as compared to a phage comprising no wild type phage coat protein from which the mutant form is derived and having a coat comprising at least one functional form of the phage coat protein.

Figure 2:
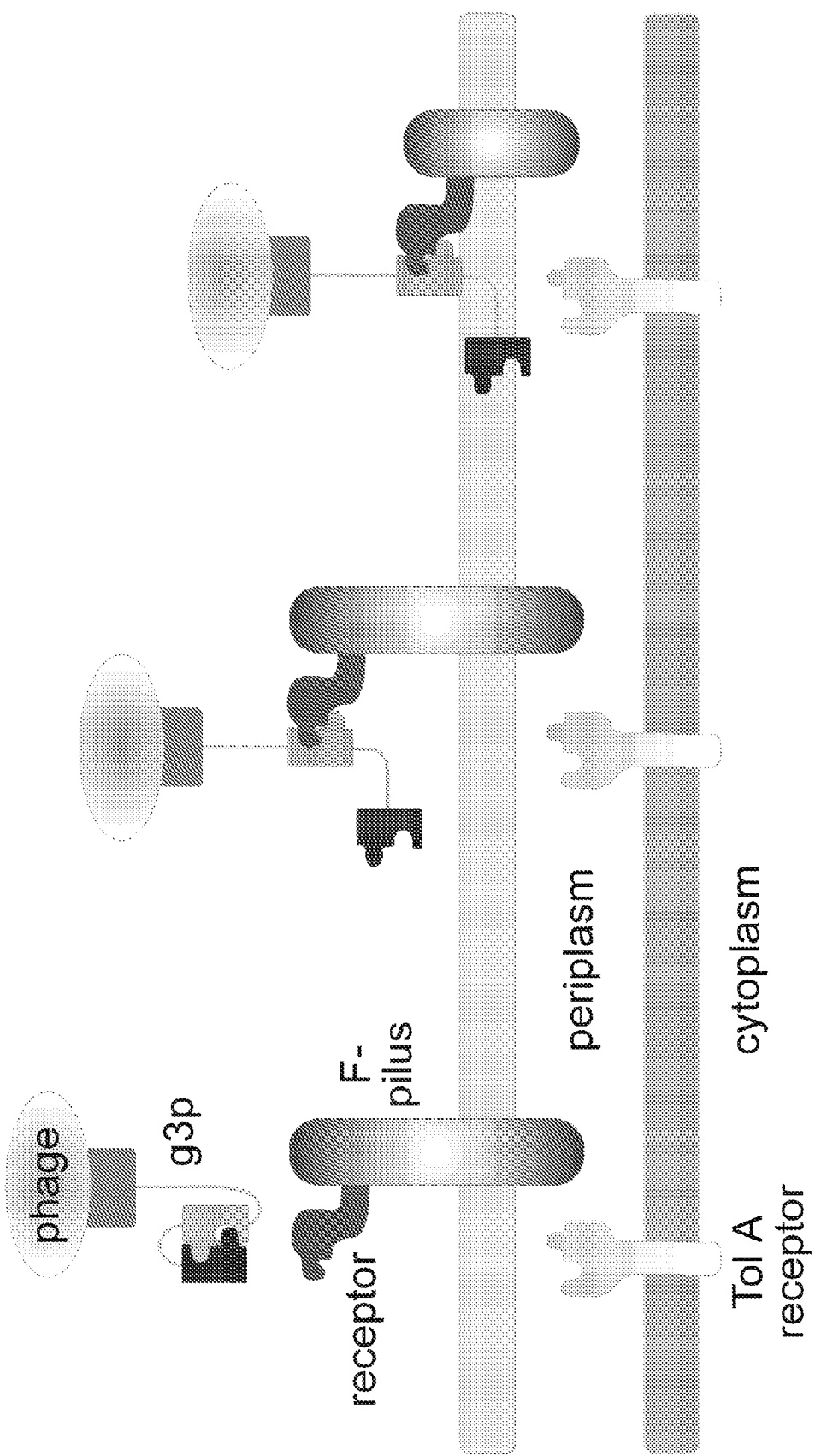
FIG. 2. Schematic representation of the interaction between the D2 domain of g3p with the F-pilus on the surface of *E. coli*, with a subsequent interaction of the D1 domain with other components of the bacterial surface.
Figure 3:
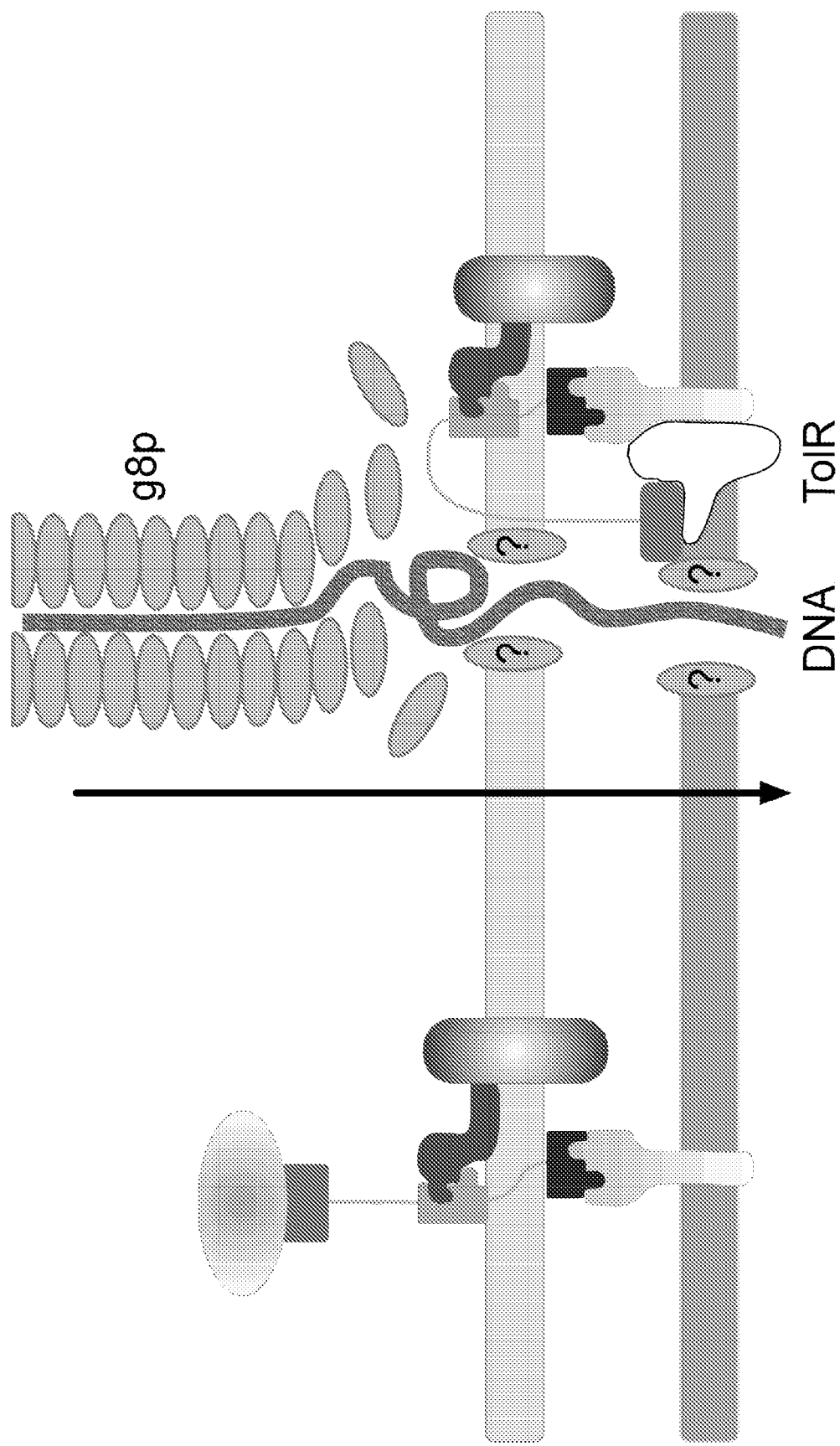
FIG. 3. Schematic representation of the interaction of the D2 domain of g3p with the F-pilus (left) and the D1 domain of g3p with the TolA receptor (see FIG. 2) and the subsequent entry (right) of the phage genome into the cytoplasm of the bacterium.
Figure 4:
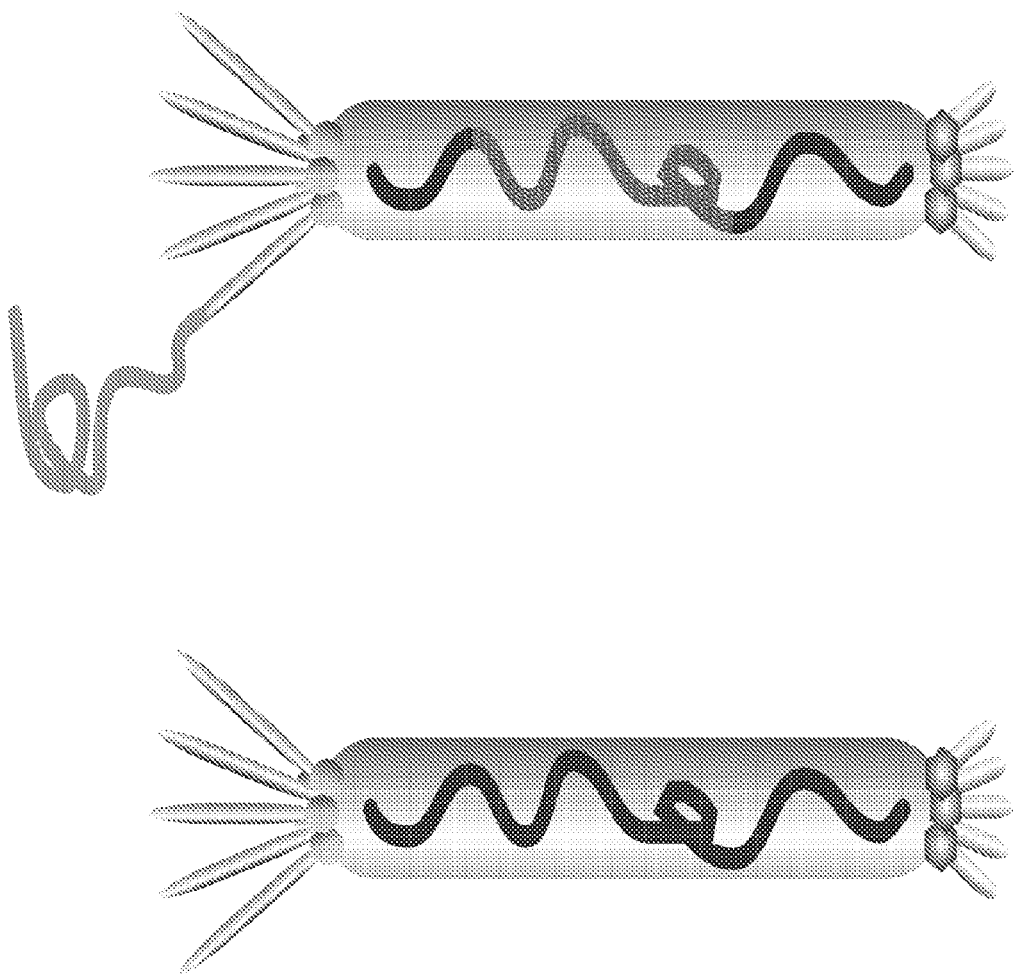
FIG. 4. Schematic representation of a wild type phage expressing five g3p's on its infectious end (left) and a recombinant phage expressing four wild type g3p's and one g3p-X fusion protein on its infectious end (right). The recombinant phage also harbors the genetic information of the fusion protein present on the surface.

In a preferred embodiment, the phage coat protein is the g3 protein (g3p) that in a wild type or functional form renders a phage to which it is attached, infectious. As is outlined in FIGS. 2 and 3, certain parts of the g3 protein are involved in the recognition of host cell receptors.

A mutant form is "impaired" in receptor binding if an alteration in the g3 protein renders the receptor to be recognized and bound by the g3 protein, or parts thereof, to a lower extent than if no alteration is present. Therefore, "impaired" as used herein means that the coat protein, such as g3p, binds the host cell receptor less efficiently, or that g3p has completely lost the ability to bind and/or recognize the host cell receptor.

In a preferred embodiment, the mutant form of the phage coat protein comprises an alteration in the g3 protein consisting of a mutation in either the D1 region, the D2 region or both.

An "alteration" or "mutation" as used herein means one or multiple point mutations, stretches of mutations, deletions, substitutions, replacements and/or swapping of parts. In a more preferred embodiment, the alteration in the g3 protein is a deletion of substantially all of the D1 and/or the D2 region. The alteration may also mean a substitution of the deleted g3 protein part by a protein or a peptide not contributing to the infectivity of the helper phage, the chimaeric phage, the infectious phage or the phage particle.

In a more preferred embodiment of the invention, a chimaeric phage or an infectious phage according to the invention comprises a nucleic acid encoding a fusion protein, wherein a proteinaceous molecule is fused to a functional form of the phage coat protein. The chimaeric phage of the invention comprises a M13, M13K07, VCSM13 or a R408 strain or a mutant, derivative or analogue strain derived from either one of these strains. A proteinaceous molecule according to the invention is fused to the functional form of the phage coat protein and comprises a protein, such as a ligand-binding moiety or an immunoglobulin (such as an antibody).

A proteinaceous molecule may also mean a peptide, such as a random stretch of amino acids or a non-random stretch of amino acids such as an antibody fragment or derivatives thereof (Fab fragment, a single chain Fv fragment (scFv), a variable region or a CDR region). A proteinaceous molecule can also mean first specific binding pair member, fusions between different kinds of (fragments of) proteins and/or fusions between (fragments of) proteins and (random and non-random) peptides, such as antibody-recognized tags.

A chimaeric phage of the invention relies on the functional form of the phage coat protein g3p and on the presence of part(s) of the phage coat protein that contribute to the infectivity of the phage for infection. The mutant form of the phage coat protein is mutated in the part(s) of the phage coat protein that render the phage infectious. The mutation is exemplified in, but not limited to, deletions, residue- or fragment substitutions, swaps and/or replacements by other protein fragments rendering it less infectious. The protein fragments may or may not be related to phage coat proteins or fragments thereof, and are essentially not capable of inducing infection of the phage particle into a host cell.

In another embodiment, the invention provides a phage collection comprising a chimaeric phage or an infectious phage according to the invention. Phages of the present invention are particularly useful for the generation of phage display libraries. Therefore, in a preferred embodiment, the phage collection is a phage display library. In a more preferred embodiment, the phage collection consists essentially of chimaeric phages or of infectious phages of the invention. A proteinaceous molecule, such as (random or not random) stretches of amino acids, peptides, protein parts or even entire proteins can be fused to the phage coat proteins and can form a first specific binding pair member. This fusion is typically done at the terminal ends of the coat protein, wherein the additions typically do not affect the function of the phage coat protein. Moreover, it also often does not interfere with the function of the added moiety. Thus, it is possible to generate libraries that can be used to locate and clone specific binding molecules. Such libraries can comprise peptides or larger molecules. Preferably, the larger molecules comprise a protein, such as an antibody or a functional part, derivative and/or analogue thereof, such as full length heavy and/or light chains from an immunoglobulin molecule, or fragments of immunoglobulins such as Fab fragments, single chain Fv (scFv) fragments, CDR regions, sole variable regions and/or combinations of the above.

In another aspect, the invention provides a method for making a phage particle which comprises the steps of providing a host cell with a first nucleic acid encoding a fusion protein. The fusion protein comprises a proteinaceous molecule fused to a functional form of a phage coat protein or to a functional part, derivative and/or analogue of the phage coat protein. The method further includes providing the host cell with a second nucleic acid encoding a mutant form of the phage coat protein, the mutant form being characterized as described above. For instance, less infectious may also mean non-infectious. The method also includes culturing the cell to allow assembly of the phage, the host cell otherwise or additionally comprising nucleic acid encoding at least all essential proteins, or functional equivalents of the essential proteins for the assembly of the phage particle.

In a preferred embodiment, the invention provides a method wherein the nucleic acid encoding at least all other proteins or functional equivalents thereof that are essential for the assembly of the phage particle in the host cell is comprised by a helper phage and the helper phage is used to deliver the nucleic acid to the host cell. In a more preferred embodiment, the nucleic acid that is delivered by the helper phage also comprises the second nucleic acid encoding the mutant form of the phage coat protein. In an even more preferred embodiment, the first and the second nucleic acids are separate nucleic acids that each may comprise separate unique selection markers to ensure that the host cell comprises at least one copy of each separate nucleic acid. The first and second nucleic acids each comprise separate unique origins of replication to ensure no interferences during replication.

In another aspect of the invention, the number of possible homologous recombination events between overlapping stretches of nucleic acid sequences between the separate nucleic acids is reduced due to the use of different codons within each nucleic acid.

Using a method of the invention, it is possible to generate phage particles that comprise at least two variants derived from the same coat protein. The present invention provides novel phage particles (chimaeric phages, infectious phages and helper phages) in which the relative number of the g3p variants (either fused to a heterologous moiety or not) present in the coat can vary. Typically, one wants to influence the relative amount of the various variants in the phage coat. To that end, it is preferred that expression of the fusion protein and/or expression of the mutant form of the phage coat protein is regulatable (controllable). Preferably, this is achieved by regulating the expression of the gene encoding the phage coat protein at a transcriptional level.

Thus, preferably, expression of the fusion protein and/or the mutant form of the phage coat protein is under the control of a promoter that is well controlled. Examples of such promoters are the lac promoter, the psp promoter and the AraC/BAD promoter, the latter being influenced by the concentration of glucose or arabinose in the medium.

Particularly advantageous is the AraC/BAD promoter. The AraC/BAD promoter is preferred because it is a promoter that is controlled in a very tight manner. This promoter is for all practical purposes silent in the presence of glucose and only slightly leaky in the absence of glucose. This means that a low concentration or absence of glucose renders the promoter active, resulting in up-regulation of the gene of interest that is under the control of the promoter. If, for example, the deletion mutant of g3 (lacking the D1 and D2 infectious regions) is under the control of such a promoter, the relative number of deletion mutants, as compared to full length (or at least functional) g3-fusion proteins, would be low when the glucose concentration is relatively high. In principle, this system results in a tight regulation of the number of deletion mutants and functional coat proteins such as g3 on the coat of a phage particle, and therefore the percentage of such coat proteins and deletion mutants can be regulated.

In addition, the activity of the AraC/BAD promoter can be regulated very tightly by the addition of arabinose to the medium. The concentration arabinose used determines the level of protein expressed in *E. coli* cells. Therefore, optimal regulation of phage coat protein content is accomplished by using this AraC/BAD promoter and by altering the culturing conditions of the host cell. The use of a promoter that is dependent on arabinose, such as the AraC/BAD promoter, instead of IPTG, such as the lac-operon, prevents possible problems that will occur due to co-encapsidation of the helper plasmid in viral particles during helper phage synthesis.

As described above, it has been shown that co-encapsidation of plasmids together with the phage genome does occur (Russel and Model. 1989; Krebber et al. 1995; Rakonjac et al. 1997). If co-encapsidation occurs with a lac driven helper plasmid, it may compete with the lac driven vectors, generally used for the phage display, resulting in the production of infectious phage particles that will not contain the g3p-X fusion product. This problem most likely does not occur when the AraC/BAD promoter is used. However, in the studies presented by the present invention, such competition problems with the lac promoter were not observed. Therefore, other regulatable promoters such as the psp and lac promoter can be used to generate phages according to the invention. It is therefore also a part of the invention to use such promoters as an alternative to the AraC/BAD promoter.

A method for the production of a phage particle is preferably used to produce a chimaeric phage according to the invention. The host can be provided with nucleic acid encoding a phage protein in any suitable way. Preferably, however, the host is provided with a helper phage according to the invention.

A helper phage according to the invention comprises nucleic acid encoding other phage proteins or functional equivalents thereof that are essential for the assembly of the helper phage, the nucleic acid further encoding a mutant form of a phage coat protein. The mutant form is characterized in that a phage comprising no wild type phage coat protein from which the mutant form is derived and having a coat comprising mutant forms of the phage coat protein and no functional forms of the phage coat protein, is less infectious than a phage comprising no wild type phage coat protein from which the mutant form is derived and having a coat comprising at least one functional form of the phage coat protein, and wherein the helper phage does not comprise nucleic acid encoding a functional form of the phage coat protein.

The phrase "other phage proteins" is meant to refer to proteins other than the functional form of the phage coat protein or the mutant form of the phage coat protein. Nucleic acid encoding the latter may be provided to the host cell in an alternative fashion. However, the helper phage may further comprise nucleic acid encoding the functional form of the phage coat protein or the mutant form or both. Preferably, the helper phage does not comprise nucleic acid encoding the fusion protein. In this way, the helper phage is uniform and may be used to produce phages that preferentially comprise nucleic acid encoding the fusion protein in the absence of nucleic acid encoding any other required helper phage protein. Thus, preferably the fusion protein and the mutant form of the phage coat protein are encoded by separate nucleic acids. Preferably, each of the separate nucleic acids comprises a unique selection marker. Preferably, the separate nucleic acids comprise non-interfering origins of replication, wherein the origins of replication do not compete with one another resulting in bacterial cells that tolerate the separate nucleic acids for the generation of new phage particles.

The art teaches that it has been very difficult to generate helper phage batches, wherein the helper phages harbor nucleic acid that encodes all essential proteins required for assembly of a phage particle in a bacterial host cell and wherein the nucleic acid lacks a gene encoding g3p. Subsequently, the art teaches that it is difficult to produce phage libraries using such helper phages. Several difficulties are known in the art that hamper a proper generation of such helper phage batches.

The present invention provides methods and means and a good combination of features such as the use of specific origins of replication, selection markers and codons in overlapping stretches of DNA, that enable the production of phage batches containing high titers of useful helper phages, that can subsequently be applied for the generation of chimaeric or infectious phages according to the invention.

Therefore, in one embodiment, the invention provides methods and means for the production of helper phages that carry functional forms and/or wild type forms of a phage coat protein in their coat, but that nevertheless lack nucleic acid encoding for the functional form and/or the wild type form of the phage coat protein. The invention provides a method for producing a helper phage comprising the steps of: providing a host cell with a first nucleic acid encoding a functional form of a phage coat protein; providing the host cell with a second nucleic acid encoding a mutant form of the phage coat protein, wherein the mutant form is characterized in that a phage comprising no wild type phage coat protein from which the mutant form is derived and having a coat comprising mutant forms of the phage coat protein and no copies of the functional form, is less infectious than a phage comprising no wild type phage coat protein from which the mutant form is derived and has a coat comprising at least one functional form of the phage coat protein; and culturing the host cell to allow assembly of the helper phage. The host cell additionally comprises nucleic acid encoding at least all other proteins or functional equivalents thereof that are essential for the assembly of the helper phage in the host cell.

Preferably, the method does not comprise the incorporation of a wild type form of the phage coat protein in the helper phage. More preferably, the phage coat protein is the g3 protein present in the coat of most, if not all bacteriophages. Preferably, the other proteins are encoded by the second nucleic acid, wherein expression of the mutant form of the phage coat protein and/or the expression of the functional form is regulated by altering the culturing conditions of the host cell and that is preferably under the control of a controllable promoter, such as the AraC/BAD, psp and lac promoter as described above.

A phage coat protein is said to be contributing significantly to the infectiousness of a phage when it allows the phage, upon incorporation in a phage, to recognize, bind and/or infect a bacterial host in a manner comparable to a wild type version of the phage coat protein.

As used herein, the terms "less-infectious" or "non-infectious" refers to a phage, carrying no functional or wild type forms of a phage coat protein, preferably g3p, and that exhibits a significant impaired, diminished infectious capability as compared to the wild type phage (particle) as determinable in, for instance, plaque assays well known to persons skilled in the art. As used herein, the terms "less-" and "non-infectious" may also refer to a decrease in host cell specificity. In general, a non-infectious phage is unable to recognize, bind and/or enter a bacterial cell as outlined for wild type phages in FIGS. 2 and 3, whereas a less infectious phage is capable of doing so with less efficiency.

Preferably, a phage having mutant forms infects the host cell with an efficiency which is less than 50% compared to a phage carrying at least a functional form, more preferably less than 10%, still more preferably less than 1%, under conditions which are otherwise comparable.

In embodiments wherein the phage coat protein comprises a g3p, the mutant form preferably comprises at least a structural part, derivative and/or analogue of the D3 region. The structural part, derivative and/or analogue comprise at least the functionality of g3p to allow assembly of stable phage particles.

"A derivative" of a protein as used herein comprises the same activity as that which the protein is derived from. When the protein is a functional form of a phage coat protein, the derivative comprises the same functionality. When the protein is a mutant form of a phage coat protein, the derivative is also a mutant form of the phage coat protein. When the protein is a mutant form of a phage coat protein that renders a phage carrying only mutant forms of the phage coat protein less infectious, the derivative also is a phage coat protein that renders a phage carrying only derivatives and/or mutant forms of the phage coat protein less infectious. Typical derivatives are proteins comprising one or more conservative amino acid substitutions. However, derivatives may also comprise insertions and/or deletions. Furthermore, derivatives may also comprise swaps of amino acids or sequences of amino acids within the same protein or between two or more related and/or unrelated proteins.

"An analogue" of a protein as used herein comprises essentially the same activity as the protein that the analogue is analogous to. When the protein is a functional form of a phage coat protein, the analogue comprises the same functionality.

Prior to the invention, it has been difficult to generate sufficient numbers of helper phages that lack a functional g3 gene or a part, derivative and/or analogue thereof in their genome, but that nevertheless are infectious for one round of infection through E. coli cells. The present invention succeeds in generating such helper phages efficiently. Such helper phages carry functional forms and/or wild type g3 proteins (g3p's) on their surface, but nevertheless lack nucleic acid encoding the functional form and/or the wild type g3 protein.

The invention further provides methods and means to generate libraries comprising chimaeric phages with the help of such helper phages. Preferably, phage display libraries are generated. More preferably, libraries display a large variety of single chain Fv (scFv) fragments. Using the means and methods of the invention, phage libraries can be generated that contain a significant higher number of infectious phages as compared to the number of non- or less-infectious phages than were described and are present in the art. At the same time the helper phages used to produce such libraries become (through an infection round in E. coli cells) essentially non-infectious, because the g3 gene is not present in an infectivity-contributing form in the phages. Thus, after infection of a bacterial host, the phages cannot spread to other bacterial cells except of course through division of the already infected host into daughter cells.

In another embodiment, such libraries are therefore also provided by the invention. The generated libraries are particularly useful for panning experiments because the titers of phages per milliliter are significantly higher than was used in the art until the present invention. Moreover, libraries of the invention display less a-specific stickiness. Thus, the libraries display less false positives than libraries in the art. Moreover, after one round of panning, only phages that display a functional form on their surface (preferably fused to a proteinaceous molecule) can be amplified in E. coli cells, while phages that do not carry any functional forms of the phage coat protein, but only carry mutant forms of the phage coat protein are essentially non-infectious and cannot be amplified on E. coli cells. Therefore, the number of remaining phages that are used for a second round of panning is significantly decreased. As a result of using the chimaeric phages of the invention present in the libraries provided by the present invention, the number of panning rounds is decreased and the number of relevant binders is obtained in a much more sufficient manner as was possible before the present invention.

In another aspect, the invention provides nucleic acids and helper phages comprising the nucleic acids that comprise genomic DNA sequences in which at least the domains of g3p that are responsible and contributing to infection are functionally removed. The invention also provides helper phage genomic DNA's in which the leader and at least the D3 domain are unaffected and fused together. The nucleic acids are preferably based on VCSM13 and M13K07 genomic sequences. Due to a lack of a functional D1 domain, phage particles produced by the nucleic acids are essentially non-infectious.

"Essentially," as used in this context, means that no spread or at least significantly less spread of the phages to other bacterial cells than the production bacterium occurs through g3p provided infectious features. This absence of spread to other bacterial cells is due to the absence of a functional form of g3p. If during production a source for wild type form or functional form of g3p is provided, produced phages can infect a bacterium. However, if the bacterium produces phages as a result of the infection then a resulting phage particle is not capable of infecting another bacterium unless again a source for infectious g3p is provided during production. A chimaeric phage or an infectious phage of the invention preferably comprises a part of g3p that ensures the generation of a stable phage particle after one round of infection in E. coli cells. To this end, the helper phage preferably comprises a nucleic acid encoding a mutant form of the g3p. Preferably, the mutant form comprises D3 or a functional part, derivative and/or analogue thereof.

A phage display library, can for instance, be generated by providing a collection of bacteria with a library of nucleic acids encoding g3p fused to a range of different proteinaceous molecules and infecting the bacteria with helper phages of the invention. In a particularly preferred embodiment, a library of phage display particles that is produced with these helper phages contains phages that do not carry any infectious parts of g3p on their surface and phages that carry one or two full length g3p-X fusions, next to non-infectious or less-infectious parts of g3p deletion proteins. Phages in these library mixtures that do not express g3p-X fusion proteins cannot infect bacteria anymore, since they were generated in the absence of infectious g3p parts that are not fused to X. X comprises a proteinaceous molecule or a fusion partner of interest such as immunoglobulins or fragments of immunoglobulins such as Fab fragments or scFv fragments.

In one aspect, the invention provides helper phages that combine the presence of a selection marker with the presence of a bacterial origin of replication (ORI) to overcome the described problems in the production of g3-minus helper phages, and subsequently for the generation of phage display libraries. The presence of such a combination ensures the production of large amounts of helper phages and/or helper genomes. g3-minus helper phages with an ORI and a resistance marker can be made from the helper phages VCSM13 and M13K07. These helper phages, unlike M13 or R408, do contain a kanamycin resistance gene from the Tn903 transposon and a P15A ORI that are both inserted in the intergenic region of the phage genome.

Another aspect of the invention, is the fact that because of this resistance gene and the presence of this particular OR1, these helper phages can grow easily in large quantities, while empty, or no plasmid- or no genome-containing bacteria are removed under the selection pressure, and that no interferences occur between ORI's from the phage genome and the helper plasmid or between ORI's from the phage genome and the display library plasmids, when both nucleic acids are present in the same bacterial host cell. VCSM13 and M13K07 contain the P15A ORI. To prevent the disappearance of the helper genome or the helper vector, the ORI's should not cause any interferences and therefore P15A derived ORI's are not used in the vector. The vector applied for the production of helper phages is the ColE1 ORI. Besides the features and effects mentioned above, the helper vector for the generation of helper phages does not carry an F1 ORI to prevent the incorporation of the helper vector in the phage particle instead of the viral genome.

The invention also provides vectors enabling a regulated expression of the mutant form and/or the functional form of g3p by the use of a regulatable promoter and that furthermore contain a resistance gene that is different from the kanamycin resistance gene present in the helper genome. This complementary resistance is here provided by the beta-lactamase (ampicillin) gene since its product is relatively stable and ensures complete killing of bacteria that do not express the gene product.

The pBAD/gIII vector (Invitrogen) can be used as a backbone vector for the production of helper vectors of the invention. Alternatively, vectors such as pUC19 can be used. Preferably, further features of these basic helper vectors are that regions of sequence homology are minimized which significantly decreases the possibility of homologous recombination.

The invention further provides the use of TOP10, LMG and/or XL1 blue bacterial host cells for the production of helper phages that contain a g3-minus genome, but are nevertheless infectious due to the g3p present on the phages because it was delivered by the helper vector. The genotype of the TOP10 and LMG bacteria ensures that they can transport arabinose into the cell but that they cannot metabolize it (genotype: araABCD– and araEFGH+). In addition, the TOP10 bacteria are recA and endA deficient which diminishes the chance of recombination and mutation. Furthermore, the TOP10 bacteria are F-, which makes them resistant to phages that might contaminate phage batches of interest.

The present invention also provides the sequence of the VCSM13 phage genome and use thereof for the purpose of phage display library construction, cloning phage and plasmid mutants useful in general molecular biology methods and means.

The present invention further provides a partially deleted g3 gene that is still present in the helper phage genome to provide stable, but essentially non-infectious helper phages that harbor infectious g3p's on their coat. The invention describes this partially deleted g3 gene, that is made synthetically by using synthetic primers in such a way that the functionally deleted g3 gene encodes the same protein on an amino acid level as compared to the other part of the g3 gene that is present in the same bacterium, but the codons that are used do not lead to homologous recombination events. Because the leader sequences in the different settings are very different, there is no need to change these regions in the helper genome, phage display vector (with the scFv encoding genes) or helper vector. In principle, it does not matter whether the g3 gene in the helper genome, in the phage display vector or helper vector has been changed as long as the two overlapping (in amino acid content) and previously homologous g3 parts that are introduced into one E. coli cell do not match.

The present invention describes the use of codon changes in the g3 gene for the production of helper phages that are infectious due to g3p's encoded by the helper, but that lack a wild type or at least an infectious g3 gene in their genome and for the production of chimaeric phages according to the invention. The use of codon changes ensures a diminished chance for homologous recombination effects that might occur during the process of helper phage generation. The invention preferably provides the use of codon changes in the g3 gene or parts thereof for the generation of phage display libraries in which the helper phage genome, that is brought into an E. coli cell together with nucleic acids encoding for g3p-X fusion proteins, is not homologous to the g3 gene present in the DNA encoding for the g3p-X fusion protein. These codon changes ensure that the chance for homologous recombination events in the generation of phage display libraries is significantly decreased through which the quality of these libraries and uses thereof are significantly improved.

EXPERIMENTAL PROCEDURES

Primers

The following primers (obtained from Genset or Invitrogen) were used in the generation of the different vectors and helper phage genomic constructs. Most restriction enzymes hardly or fail to digest DNA if their corresponding palindrome is near the end of the DNA. Therefore, a stretch of 8 nucleotides was added to the 5' end of the D3, g3-minus and g3 ORF primers in which this stretch is an A/T rich non-hybridising 8-mer.

```
D3 primers
D3 BamHI Forward
                                          (SEQ ID NO:1)
5'-GGATCCTCTGGTTCCGGTGATTTTGATTATG-3'

D3 BamHI Backward
                                          (SEQ ID NO:2)
5'-GGATCCAGCGGAGTGAGAATAGAAAGGAAC-3' g3-minus primers
g3 minus HindIII Forward
                                          (SEQ ID NO:3)
5'AAGCTTCTGCGTAATAAGGAGTCTTAATCATGC-3' g3 minus HindIII Backward
                                          (SEQ ID NO:4)
5'-AAGCTTGTTGAAAATCTCCAAAAAAAAGC-3' g3 ORF primers
g3 ORF NcoI Forward
                                          (SEQ ID NO:5)
5'-CCATGGCTGAAACTGTTGAAAGTTGTTTAGC-3' g3 ORF XbaI Backward
                                          (SEQ ID NO:6)
5'-TCTAGATTAAGACTCCTTATTACGCAGTATG-3'

CT and N2CT primers
SnaBIclon
                                          (SEQ ID NO:7)
5'-TTAGGTTGGTGCCTTCGTAG-3'

Bamlead
                                          (SEQ ID NO:8)
5'-GGATCCAGCGGAGTGAGAATAGAAAGG-3'

BglN2
                                          (SEQ ID NO:9)
5'-AGATCTGGTACTAAACCTCCTGAGTACGG-3'

BamCT
                                          (SEQ ID NO:10)
5'-GGATCCTCTGGTTCCGGTGATTTTGATTATG-3'

PacIclon
                                          (SEQ ID NO:11)
5'-TTGCTTCTGTAAATCGTCGC-3' pUC-g3 primers
H3leadA
                                          (SEQ ID NO:12)
5'-CAAATTCTATTTCAAGGAGACAGTCATAATGAAAAAATTATTATTCG
CAATTCCTTTAG-3
```

-continued

H3leadB
(SEQ ID NO:13)
5'-GATTACGCCAAGCTTGCATGCAAATTCTATTTCAAGGAGA-3' p3endEco
(SEQ ID NO:14)
5'-GCTAACATACTGCGTAATAAGGAGTCTTAAGAATTCCAGTTCTTT-3'

PCR Reactions and Product Isolation

PCR reactions with D3, g3-minus and g3 ORF primers were as a standard (except for the elongation time of the DNA synthesis cycle step) performed using the following 50 µl hot start PCR scheme and the AmpliTaq PCR kit from Perkin Elmer: 1 µl 10 mM dNTP (Roche Diagnostics), 4 µl 25 mM MgCl$_2$, 5 µl 10×PCR buffer supplied with the kit, 5 µl 2.5 µM Forward primer, 5 µl 2.5 µM Backward primer, 0.3 µl 5 units/µl AmpliTaq, 10-50 ng template, sterile bi-distilled water. All components were kept on ice until placing in the pre-heated PCR block. The standard program was as follows. 12 cycles of 25 sec at 94° C., 52° C. annealing for 25 sec, 72° C. polymerization ending with one cycle of 72° C. for 7 min followed by storage at 4° C. The time of polymerization for new helper genome synthesis was 12 min, and for g3 amplification and for AraC gene and AraC/BAD promoter amplification this was set at 90 sec. PCR reactions with pUC-g3 primers were performed as above, but with Pwo polymerase (Boehringer Mannheim) instead of AmpliTaq, and with the following program: 30 cycles of 45 sec at 94° C., 50° C. annealing for 30 sec and 72° C. polymerization for 1 min, ending with one cycle of 68° C. for 8 min followed by storage at 4° C. PCR reactions with CT and N2CT primers were performed as above, but with Taq polymerase (Gibco) instead of AmpliTaq, and with the following program: 25 cycles of 30 sec at 96° C., 53° C. annealing for 30 sec and 72° C. polymerization for 2 min, ending with one cycle of 72° C. for 10 min followed by storage at 4° C. An exception was the PCR reaction with N2CT primers BglN2 and PacIclon, which was performed using Taq DNA polymerase recombinant (Invitrogen) with the following program: 30 cycles of 45 sec at 94° C., 55° C. annealing for 30 sec and 72° C. polymerization for 2.5 min, ending with one cycle of 72° C. for 10 min followed by storage at 4° C.

All PCR products were separated on 0.5%-1% TBE agarose gels containing 100 ng/ml ethidium bromide. After imaging, the desired fragments were cut out using sterile disposable chirurgical knives and isolated with Qiagen's gel purification kit according to the guided protocol.

Ligation Reactions

Ligation reactions were as a standard performed in the following reaction mixtures:

50 ng vector or helper genome
25 ng insert
4 µl 5× ligation buffer (Gibco BRL)
1 µl T4-ligase (Gibco-BRL, 200 units/µl)
sterile bi-distilled water to 20 µl.

However, for the construction of the pUC-g3 helper plasmid, T4 DNA ligase (Roche, 1 unit/µl) was used, while T4 DNA ligase (NEB, 400 units/µl) was used in the construction of the helper phage genomes CT, N2CT and p3-minus. The mixtures were incubated overnight at 6-16° C. Then, 30 µl sterile water, 5 µl K-acetate 3M pH 4.8 acidic acid adjusted (KAc), 1 µl glycogen 10 mg/ml and 50 µl isopropanol or 96% ethanol were added and mixed thoroughly. After 15 min of precipitation, the tubes were centrifuged at maximum speed at 4° C. for 10 min. The pellet was once washed with 1 ml 70% ethanol and after drying, dissolved in 10 µl sterile water. Half of this volume was used for electroporation together with 50 µl competent cells.

Sequencing

Sequencing of the clones was performed according to the instruction guide sent along with the ABI PRISM BigDye Terminator Cycle Sequencing Kit (Applied Biosystems) at 50° C. annealing temperature. All clones were sequenced in order to verify the correctness of the products. The sequence of the VCSM13 helper phage genome was determined by the primer-walking method on both strands, a method generally known to persons skilled in the art.

Electroporation

All bacterial strains, except those that were used for the helper phage production, were acquired from manufacturers as electroporation competent cells with the highest competence available and transformed according to the manufactures protocol using 0.1 cm cuvettes (BioRad). The production of helper phages, however, is dependent on TOP10 or LMG cells (Stratagene) containing the helper plasmid (pBAD/gIII-g3). These cells were made competent and stored at −80° C. until use as follows: One colony of the bacteria was used to inoculate in 10 ml 2×TY with ampicillin (100 µg/ml) and for LMG also with tetracycline (10 µg/ml) and cultured by vigorously shaking at 30° C. overnight. Next, the cultures were spun down at 3000 rpm for 5 min. The pellet was resuspended in 500 ml fresh 2×YT including the antibiotics and cultured until OD 0.5 in a 2 l Erlenmeyer flask on a shaking platform at 37° C. These cells were allowed to cool on ice water for 45 min and centrifuged in pre-cooled buckets and rotor at 3000 rpm at 4° C. for 25 min in a Sorvall centrifuge using a GLA-3000 rotor. The supernatant was discarded and the cells were slowly and carefully resuspended in 100 ml ice-cold 10% glycerol. The centrifugation and glycerol steps were repeated twice. The final pellet was taken up very carefully in 5 ml 10% ice-cold glycerol and aliquoted in pre-cooled eppendorf tubes. Next, these tubes were immersed in a mixture of ethanol and dry ice for 5 min to ensure very quick freezing of the cells. The tubes containing the electrocompetent cells were stored at −80° C. until use. A comparable procedure was used to make competent cells of XL-1 (Stratagene) containing the helper plasmid pUC-g3.

Phage Production

The desired F$^+$ E. coli strain is inoculated in 2×YT medium containing the required antibiotics and cultured at 37° C. at 220 rpm until OD 0.2. The (helper-) phage is added to the culture and incubated for 30-45 min at 37° C. in a non-shaking waterbath. Then, kanamycine (50 µg/ml) is added to the cells and cells are further incubated at 220 rpm at 37° C. for 30-45 min. Subsequently, this solution is spun at 3500 rpm at room temperature for 15 min. The supernatant is removed carefully and the pellet is brought to the desired volume of 2×YT medium containing all required antibiotics. Cells are cultured overnight at 30° C. for a phage display library and at 37° C. for regular (helper-) phages on a shaking platform.

Titer Determination

One colony of Xl1 blue (Stratagene) is inoculated in 5 ml 2×YT containing 10 µg tetracycline per ml (YT-T) in a 50 ml tube (Falcon) and cultured at 37° C. at 220 rpm overnight. 200 µl of this culture is added to 5 ml YT-T and cultured until OD 0.2. Then, the phage stock is diluted in YT and a dilution series as required is made to determine the number of plaque forming units. For each dilution step, 100 µl of the O.D. 0.2 XL1 Blue culture is taken and added to 100 µl of the phages. This mixture is incubated for 25 min at 37° C. in a water bath (not shaking). The 200 µl of bacterial cells is pipetted onto a 2×YT-broth plate containing the required antibiotics. The suspension is spread using a sterile glass rod. After drying, the plates are inverted and transferred into a 37° C. incubator. After overnight culture, the number of colonies are counted. Each colony indicates the presence of 1 infective phage particle in the original phage solution. The number of infectious particles per ml of the analyzed stock is calculated. The phage particles are ELISA tested according to the protocol supplied with anti-M13 and anti-M13-HRP conjugate (Pharmacia).

Isolation of DNA from Phages

An overnight phage culture is grown as described above. If a large scale isolation of DNA was required the BioRad Plasmid Maxi Prep kit was used according to the manufactures instructions, except for the elution step which is done with 10 mM Tris pH8.5 at 65° C. for 10 min. Small or medium scale isolations were performed using Qiagen's mini-prep kit according to the instruction supplied with the kit except for the elution step. The elution step was performed at 65° C. for 10 min.

Peg Precipitation

The medium containing bacteria and phages is collected in 450 ml buckets. The mixture is spun in a pre-cooled Sorvall centrifuge using a GSA-3000 rotor at 8000 rpm for 20 min. Then, 90 ml 20% PEG/2.5 M NaCl is pipetted into clean 450 ml buckets. 360 ml of the supernatant of the centrifuged medium containing the phages is brought into the PEG containing buckets and mixed well. The mixture is set on ice water for 2 h or overnight in the fridge. The precipitate is pelleted by centrifugation in a pre-cooled Sorvall centrifuge at 8000 rpm for 20 min. The supernatant is decanted and the buckets are left to drip out for 5 min in order to remove as much Precipitation buffer as possible. Subsequently, 32 ml PBS/1% bovine serum albumin (BSA) is added to the 450 ml buckets containing the pelleted phages and buckets are rotated on a bottle roller for 15 min. The solution is transferred to a SS-34 compatible centrifuge tube and spun in a pre-cooled Sorvall centrifuge containing a SS-34 rotor (or equivalent equipment) for 25 min at 13,000 rpm. This step removes all kind of debris and small bacteria. In the meantime, the plunger is removed from a 50 ml syringe and attached to a 0.45 µM filter (Whatmann). The centrifuged supernatant is transferred into the syringe and pushed through the filter. This step removes all small bacteria and other cells. 8 ml 20% PEG/2.5 M NaCl is added and mixed well. The tubes are set on ice for 1 h. The high-speed centrifugation step is repeated as described above. The supernatant is decanted and the tube is let to drip out on a paper towel for 5 min. The phage pellet is dissolved in 5 ml PBS/1% BSA. Then, 5 ml 100% glycerol is added to the phage solution and mixed well. Phages are stored at −20° C. Typically, the solution contains approximately 2 to $5 \times 10^{13}$ infectious phage particles per ml.

Examples

To illustrate the invention, the following examples are provided, but are not intended to limit the scope of the invention.

Example 1

Cloning of the pBAD/gIII-g3 helper vector.

Figure 5:
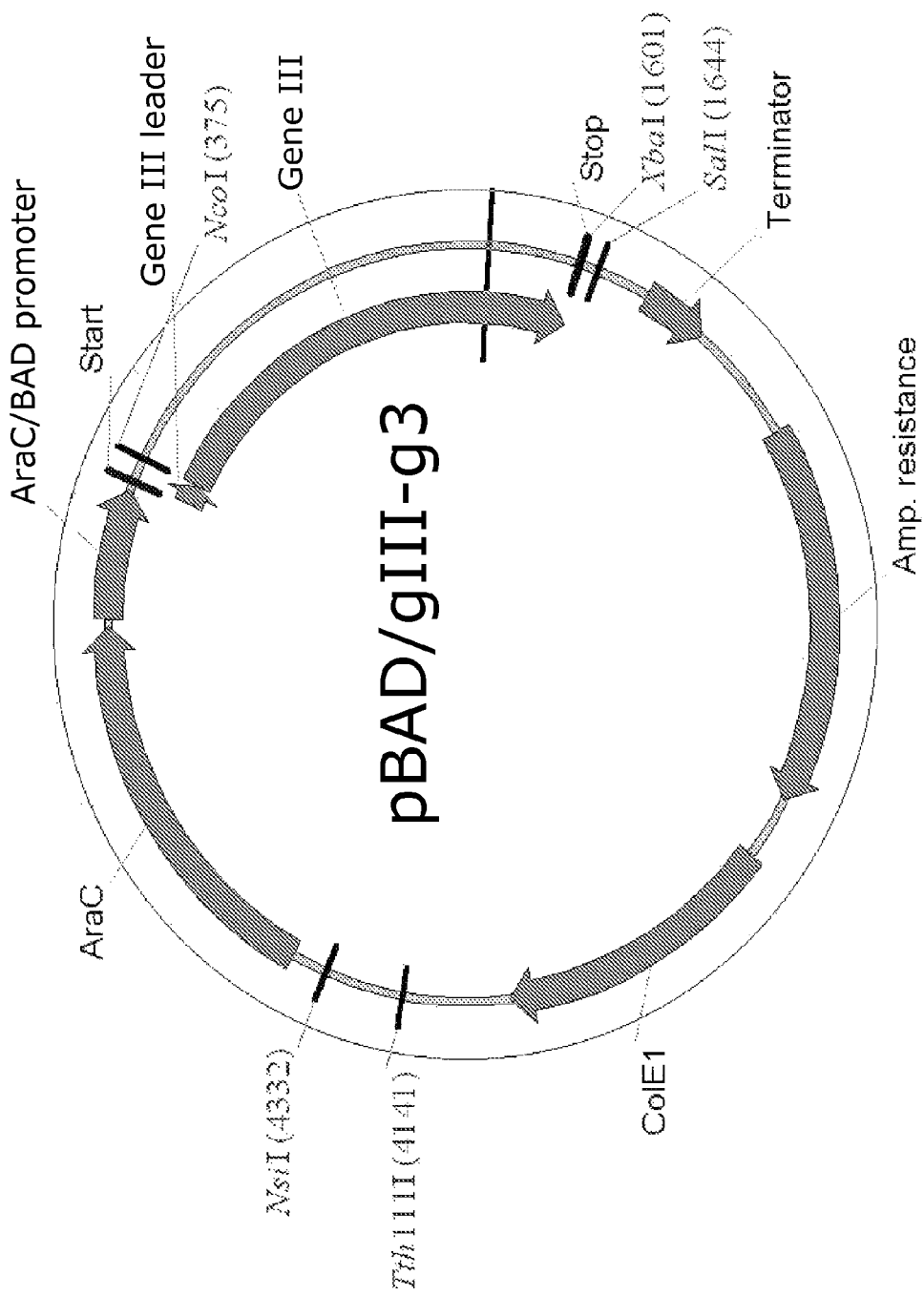
FIG. 5. Schematic representation of the pBAD/gIII-g3 helper vector harboring the full-length g3 gene under the control of the AraC/BAD promoter and further harboring an ampicillin resistance and a ColE1 origin of replication (ORI).

The full Open Reading Frame (ORF) of the g3 gene was generated by using M13K07 (Gibco-BRL) DNA as a template in a standard PCR reaction together with g3 ORF NcoI Forward (SEQ ID NO:5) and g3 ORF XbaI Backward (SEQ ID NO:6) primers. The purified PCR product and the pBAD/gIII vector were both digested with NcoI (NEB) and XbaI (Roche Diagnostics) simultaneously in buffer H (Roche Diagnostics) for 4 h at 37° C. After ligation, isolation, electroporation in TOP10 (Stratagene) and LMG (Stratagene) cells, two correct clones were selected by sequencing and grown on a large scale followed by the isolation of the DNA. The DNA was reprecipitated with 70% ethanol and in the presence of KAc and the pellet was washed twice with 70% ethanol. After drying, the DNA was dissolved in sterile bi-distilled water and stored at −20° C. until use. The resulting plasmid pBAD/gIII-g3 is depicted in FIG. 5. This helper vector contains the full sized g3 gene under the control of the AraC/BAD promoter, ampicillin resistance gene and a ColE1 ORI as most important features.

Example 2

Cloning of the g3-minus helper phage genome.

Figure 6A:
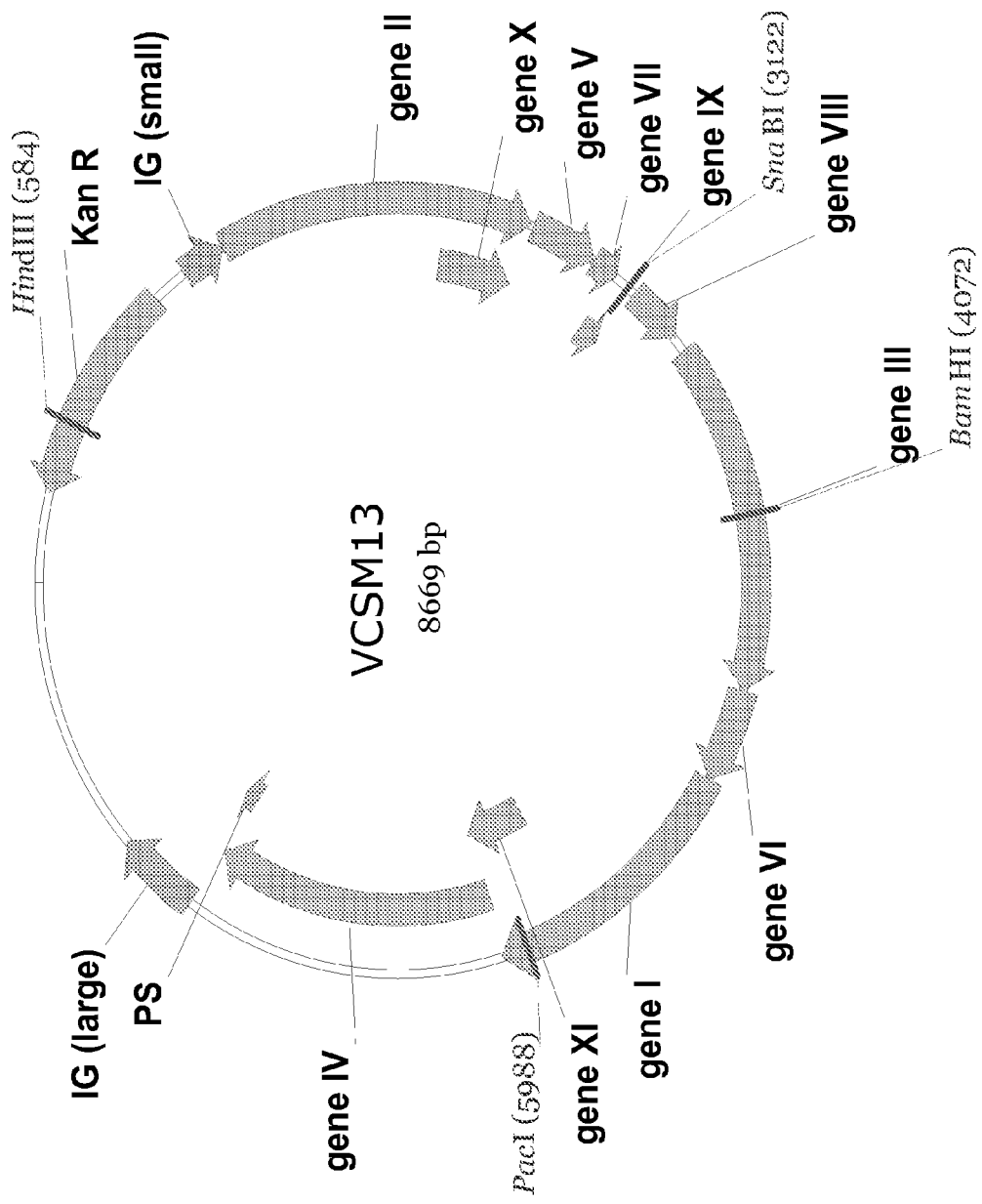
Figure 6B:
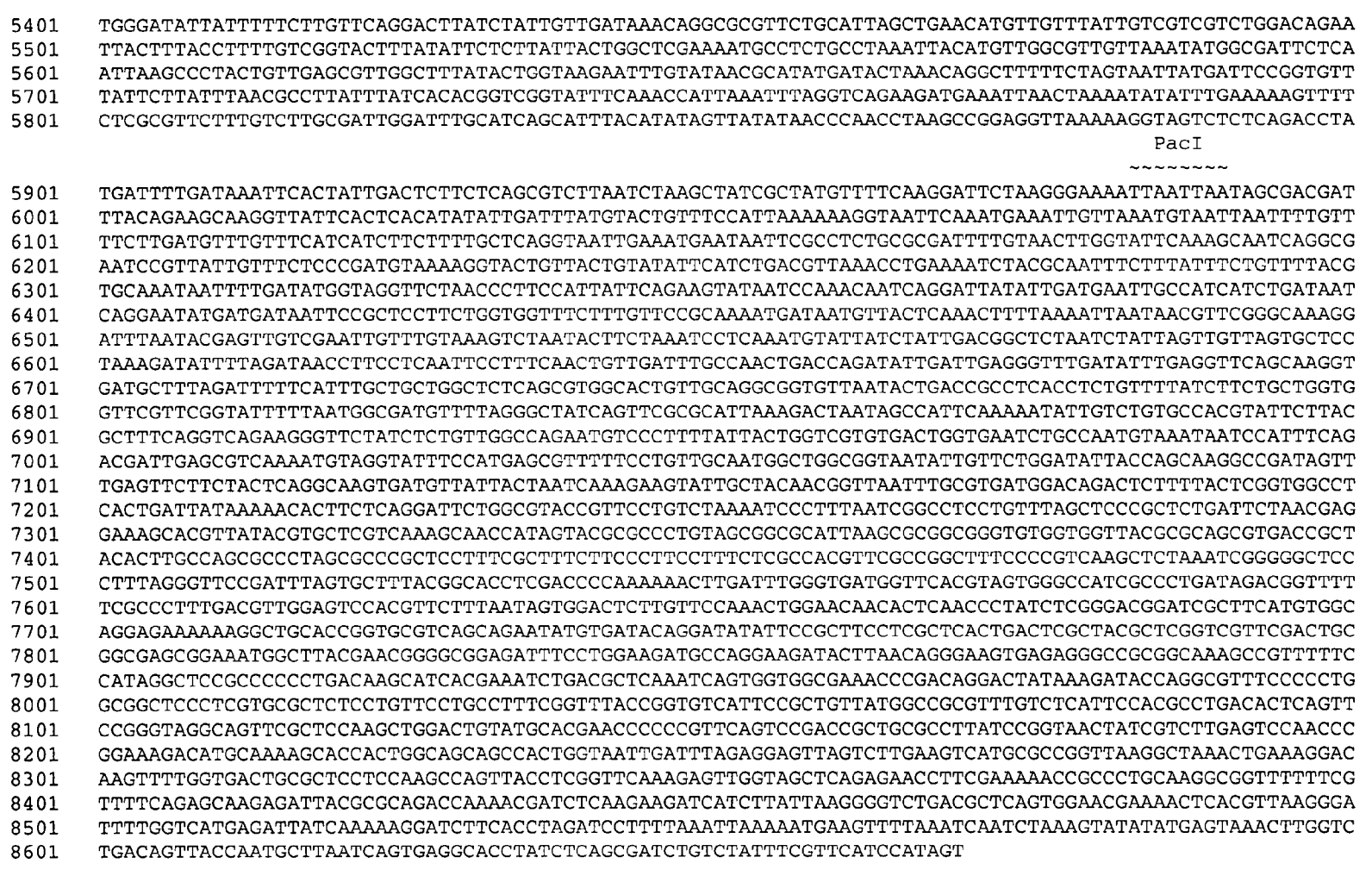

VCSM13 (Stratagene) is a widely used helper phage, however, its sequence is not publicly available. The full DNA sequence of the VCSM13 genome was determined and is depicted schematically in FIG. 6A and in nucleotide order in FIG. 6B. The use of g3 minus HindIII Forward (SEQ ID NO:3) and g3 minus HindIII Backward (SEQ ID NO:4) primers and M13K07 and VCSM13 as templates in a standard PCR reaction resulted in the formation of a PCR product that contained HindIII sites at both ends of the DNA. After separation, gel isolation and purification, digestion with HindIII (Roche Diagnostics) and re-purification of the DNA, the product was self-ligated under standard ligation conditions and the resulting helper phage genome, named g3-minus, was electroporated into XL1 Blue cells (Stratagene).

The transformed cells were resuspended in 5 ml 2TY medium and cultured shaking at 37° C. for 1 h. Kanamycin was added to an end-concentration of 50 µg/ml and the cells were allowed to grow at the same conditions for another 5 h. The culture was centrifuged at 3000 rpm for 15 min and the supernatant passed through a 0.22 µM filter to remove bacteria. At the same time, a culture of exponentially growing XL-1 Blue bacteria was prepared. Fractions of the filtrate (50-1000 µl), containing phage particles, were added to 5 ml of XL-1 Blue bacteria and incubated at 37° C. for 30 min without shaking. The culture was centrifuged again, the supernatant discarded and the cells were plated on 2×YT-K-T plates and transferred into an incubator at 37° C. for overnight growth.

Figure 6C:
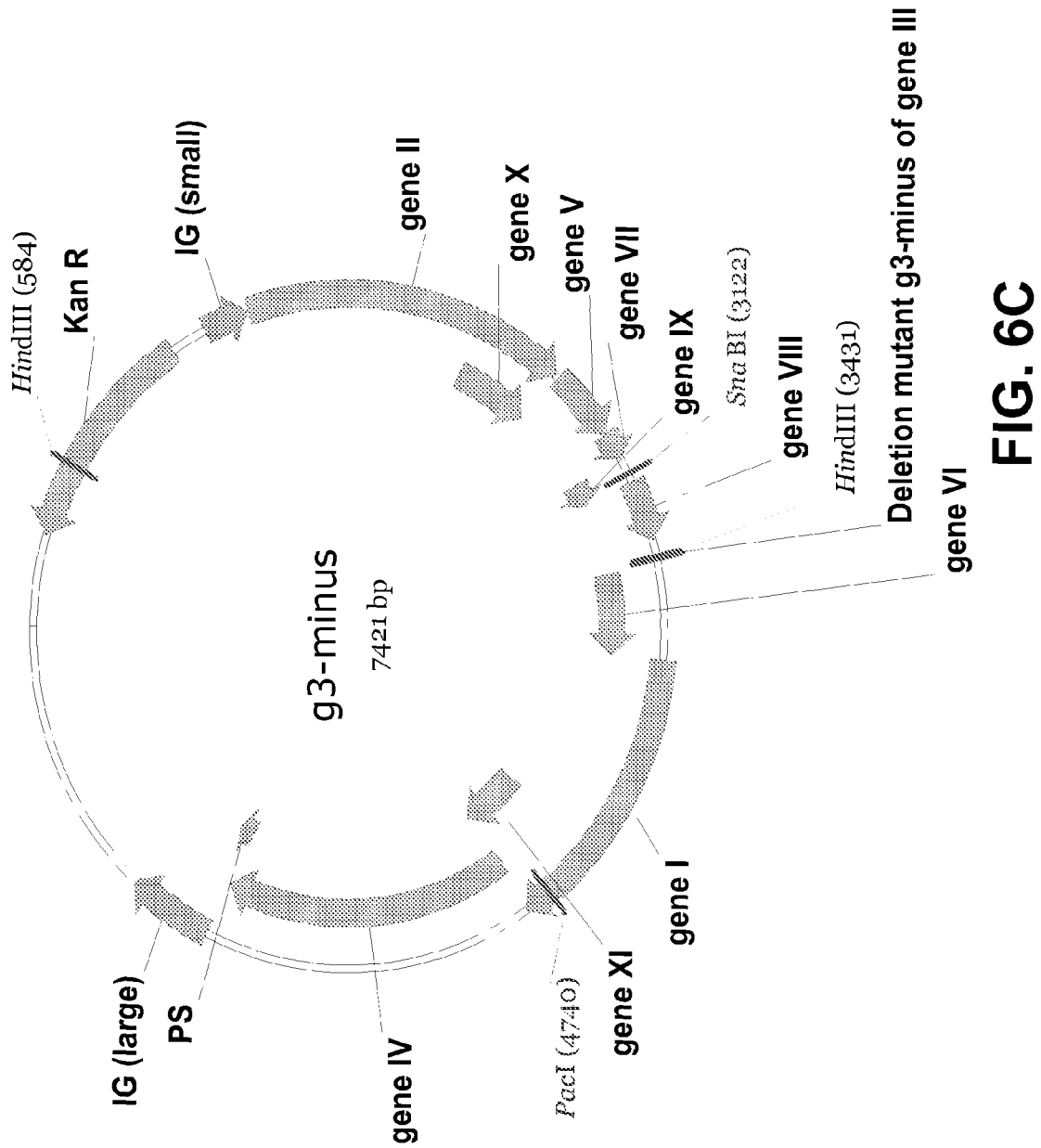

Eight correct clones that lack the g3 ORF (checked through the BamHI site) and include the introduced HindIII site were isolated and used for g3-less helper phage production in the presence of the pBAD/gIII-g3 helper plasmid. Two clones that were able to form phages in the presence of the helper plasmid were kept. From these clones, a large quantity of DNA was isolated and stored for further experiments. The obtained VCSM13-derived g3-minus helper phage genome, in which the entire g3 gene except for the last six codons was replaced by a HindIII site, is depicted schematically in FIG. 6C, while the g3-minus sequence is depicted in FIG. 6D.

Example 3

Cloning of the D3 helper phage genome with a partially deleted g3 gene.

Figure 7A:
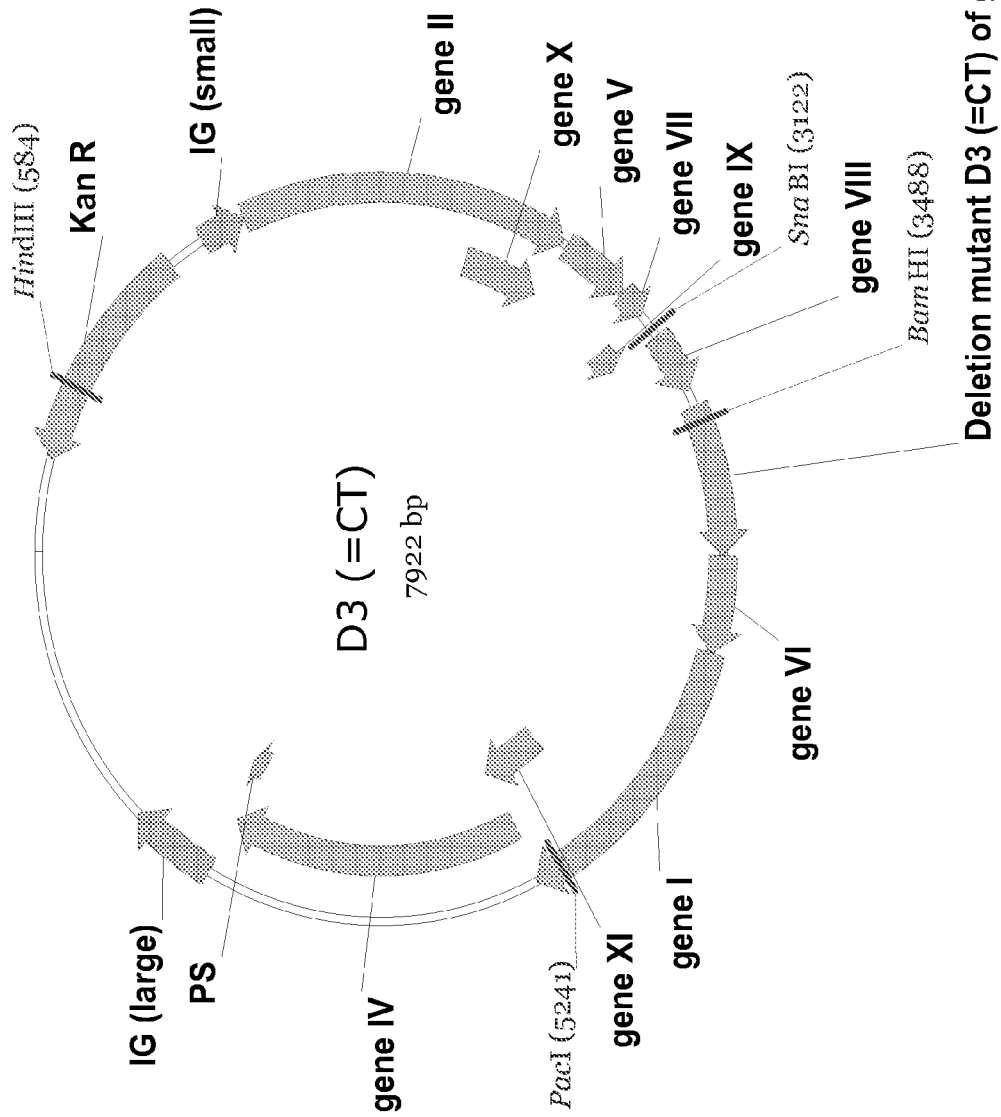

The construction of helper phage genome that express only the D3 part of the g3 gene was comparable to the above described g3-minus helper phages with the exception that the primers used were D3 BamHI Forward (SEQ ID NO: 1) and D3 BamHI Backward (SEQ ID NO:2) primers in order to generate the new genome. All other procedures were the same as for the g3-minus procedure, except for the use of BamHI instead of HindIII. In the end, the DNA of two correct clones was kept and stored at −20° C. The final VCSM13-derived construct of the helper phage genome (named D3: it only expresses this part of the g3 gene that does not contribute to the infectiousness of the phage particle) is depicted in FIG. 7A, while the D3 sequence is depicted in FIG. 7B.

Example 4

Production of infectious helper phages that do not carry a gene encoding the wild type g3p.

The procedures for generating g3-less and generating partially deleted g3 (or D3 expressing) helper phages are identical. Frozen competent TOP10 or LMG cells that contain the pBAD/gIII-g3 helper plasmid were electroporated using 100 ng helper phage DNA. After recovery, the cells were transferred into 4×250 ml 2×YT-K-A medium supplemented with 0.05% arabinose (Sigma). Phages were produced during overnight culture at 37° C. and vigorous shaking. The next day the phages were purified and stored according to the standard procedures of precipitation and storage that were described supra. The number of infectious particles and the number of phages were determined by titration and ELISA procedures that were also described supra. For g3-less helper phages, approximately $5 \times 10^{11}$ infectious particles were synthesized while for D3 approximately $5 \times 10^{13}$ infectious phages were formed using these procedures.

Example 5

Amplification and harvesting of phage display libraries containing infectious phages carrying g3p-scFv fusions and non-infectious helper phages, using g3 minus and partially g3 deleted helper phages.

A frozen library was inoculated as follows. In general, approximately 5-10 µl concentrated stocks were inoculated in 25 ml 2×YT containing the required antibiotics and 5% glucose and grown at 37° C. with vigorous shaking. At OD 0.3-0.4 (after about 2-3 h), a 500-1000 fold excess of helper phage was added. The medium containing the helper phages and bacteria was incubated in a water bath at 37° C. without shaking for 25 min. Removal of dead cells and excess of phage particles was realized after a centrifugation step at 3000 rpm for 15 min. The pellet was resuspended in 250 ml 2×YT with antibiotics but without glucose and grown at 30° C. with good aeration overnight. The next day the formed phages were isolated and stored using the standard PEG/NaCl procedure.

Example 6

Codon usage in g3 and the partially deleted g3 gene (D3) to prevent homologous recombination during helper phage production and library amplification.

In order to prevent possible recombinations between a genomic nucleic acid encoding the helper phage g3 protein region (or a part thereof such as the D3 domain) and other nucleic acids (like the phage display vector and the AraC/BAD helper vector), a series of helper phages are designed that contain changed codons within the g3p region. Newly translated g3p's are identical to the wild type g3 protein or protein part (D3). Due to these changes, g3-ORF coding DNA domains cannot or barely recombine with the phage display vectors or the AraC/BAD-g3 helper vector. The codons that are used to generate non-homologous g3 genes are depicted in FIG. 8 and are optimal for the *E. coli* transcription machinery. PCR generation of helper phage genomes (VCSM13, M13K07, D3, g3-minus or AraC/BAD) with g3-leader backward and g3 end forward primers with NotI restriction sites ensure the generation of PCR products containing all helper phage components and genes, except for the g3 ORF. New g3 regions are constructed with overlapping primers and are inserted in helper phages. The PCR-generated g3p or parts thereof are digested with NotI and ligated in the NotI digested PCR generated helper phage genome. After transformation and selection of correct helper genomes (with a new g3 gene), helper phages are grown as described.

Example 7

Selection of thyroglobulin-interacting phages using a library amplified with helper phages comprising only the D3 part of g3p in their genome.

In order to validate the D3 helper phages in standard phage selections, a selection was performed using an antibody phage display library that was amplified using the D3 helper phages as described above. Procedures that were used were essentially as described by De Kruif et al. (1995a). Briefly, thyroglobulin was coated to a plastic tube. The tube was blocked in PBS containing 2% milk (MPBS) whereafter the antibody phage display library, also blocked in MPBS, was added to the tube. The phages were allowed to bind for 2 h, whereafter non-binding phages were removed by washing the tube in PBS containing 0.1% Tween-20 as described by De Kruif et al. (1995a). The binding phages were eluted in 50 mM Glycin/HCl pH 2.2 (10 min at RT) and used to infect freshly grown XL-1 Blue bacteria. The bacteria were plated on 2TY agar plates containing the appropriate antibiotics and glucose, incubated overnight at 37° C. and used to prepare an enriched phage display library; phage D3 was again used as helper phage. The procedure was repeated once, whereafter individual *E. coli* colonies were used to prepare monoclonal phage antibodies. These monoclonal phage antibodies were tested in ELISA for their ability to bind specifically to the thyroglobulin antigen. Results show that after two rounds of selection, 25/46 colonies show positive binding to thyroglobulin. Previously we found that by using a general VCSM-13 as a helper phage, at least 3 rounds of selection were required to obtain specific binders in this selection format.

Example 8

Selection of phages interacting with myeloma cells using a library amplified with helper phages comprising only the D3 part of g3p in their genome.

In order to validate the D3 helper phages in selections on intact cells, a selection was performed using an antibody phage display library that was amplified using the D3 helper phage. Procedures that were used were essentially as described by De Kruif et al. (1995a and 1995b).

Briefly, myeloma cells (AML, CD33+, CD34+) were obtained from the blood of a patient undergoing treatment at the Utrecht University Hospital (The Netherlands). 0.5 ml phage library was added to 3 ml RPMI medium containing 10% FCS (RPMIS) and incubated on ice for 15 min. The myeloma cells were added and the cell suspension was rotated at 4° C. for 2 h. The cells were washed 5 times in 50 ml ice-cold RPMIS whereafter the binding phages were eluted (in 50 mM Glycin/HCl pH 2.2 for 10 min at RT) and used to infect freshly grown XL-1 Blue bacteria. The bacteria were plated on 2TY agar plates containing the appropriate antibiotics and glucose, incubated overnight at 37° C. and used to prepare an enriched phage display library. Again, the D3 expressing helper phages were used as helper. The procedure was repeated once, whereafter individual *E. coli* colonies were used to prepare monoclonal phage antibodies. These monoclonal phage antibodies were tested in FACS procedures for their ability to bind myeloma cells. Results show that 23 out of 41 clones tested bound specifically to epitopes expressed on the myeloma cells. Generally, three or more rounds of selection are required to obtain similar numbers of binding phages using identical procedures, with the exception of using VCSM-13 helper phages instead of the helper phages described by the invention.

Example 9

Figure 9:
FIG. 9. Schematic representation of the pUC-g3 helper plasmid harboring the full length g3 gene under the control of the lac promoter and further harboring an ampicillin resistance gene (Amp R) and a ColE1 origin of replication (ORI).

Cloning of the pUC-g3 helper plasmid.
As an alternative to the pBAD/gIII-g3 helper plasmid described above, a pUC19-based helper plasmid for the expression of wild-type g3p under the control of a lac promotor was constructed. The use of H3leadA and p3endEco primers and VCSM13 as a template in a PCR reaction detailed above resulted in the formation of a PCR product containing the g3 gene sequence with 28 additional nucleotides upstream of the gene and 15 additional nucleotides including an introduced EcoRI site downstream. The use of H3leadB and p3endEco primers and this PCR product as a template in a PCR reaction detailed above resulted in the formation of an extended PCR product containing the g3 gene sequence, with introduced HindIII and EcoRI sites upstream and downstream of the gene, respectively. The extended PCR product was cloned into plasmid pCR4-BluntII-TOPO using the Zero Blunt TOPO PCR Cloning Kit (Invitrogen) and the sequence of the insert was checked. Plasmid pUC19 (New England Biolabs) and the pCR4-BluntII-TOPO derivative containing the g3 gene were both digested with HindIII and EcoRI. The fragment containing the g3 gene from the pCR4-TOPO derivative and the vector fragment of pUC19 were purified from gel and ligated. The resulting plasmid, named pUC-g3, was electroporated into XL-1 cells (Stratagene) and a correct clone was selected by sequencing DNA isolated from the transformed cells. Helper vector pUC-g3, which contains the g3 gene under the control of the lac promotor, is depicted schematically in FIG. 9.

Example 10

Figure 10:
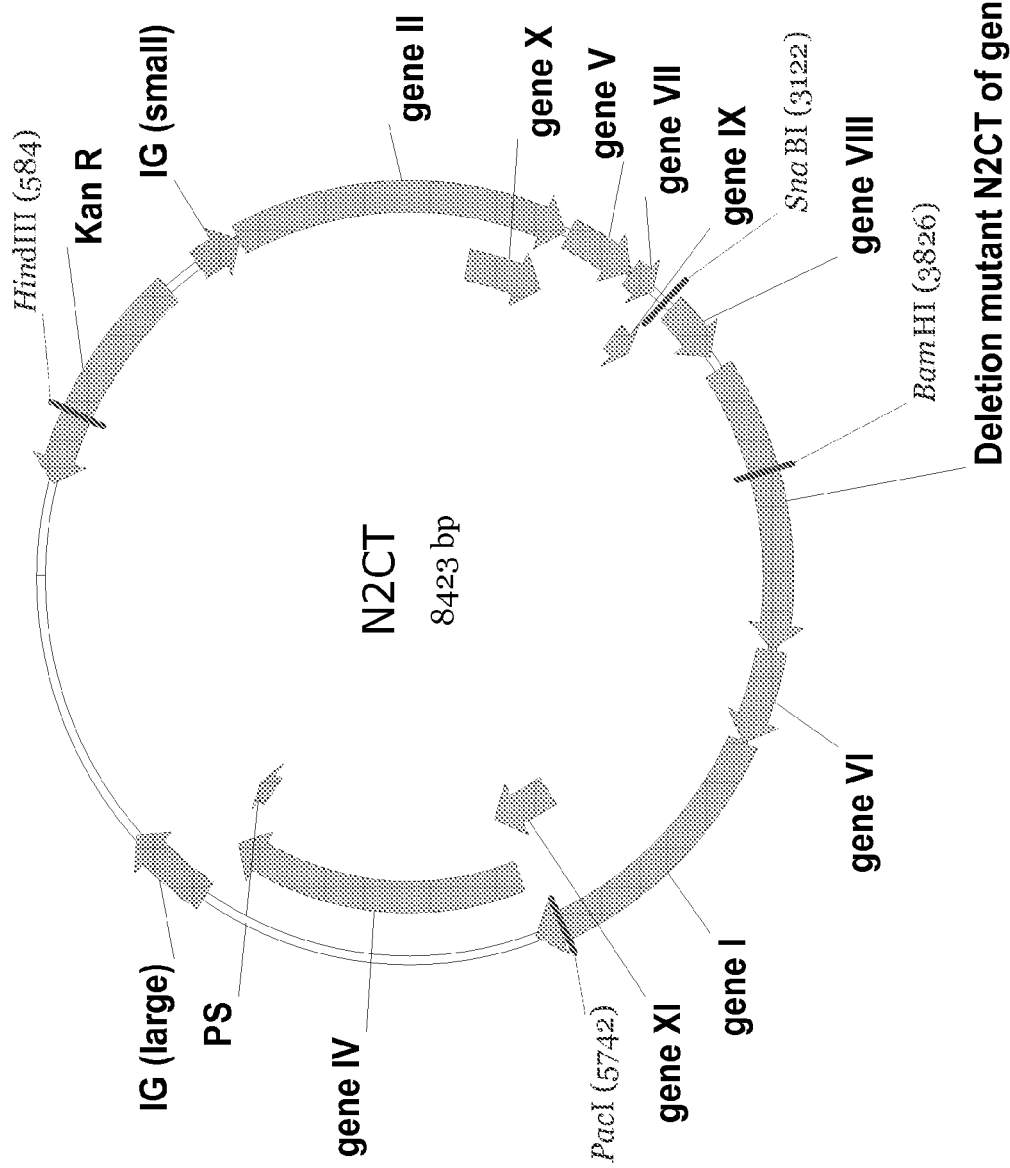
FIG. 10. Schematic representation of the VCSM13-derived N2CT helper phage genome deleted for the NI (D1) domain of the g3 gene that confers infectivity to the phage.

Alternative Cloning of Helper Phage Genomes with a Partially Deleted g3 Gene
In the cloning procedures described in example 2 and 3, a very large region of the phage genome is amplified by PCR, with the risk of introducing artificial mutations due to the limited fidelity of DNA polymerase. An alternative strategy was applied to produce helper genomes with a partially deleted g3 gene.
In this strategy, a part of the g3 sequence encoding the g3 leader, and a part of the g3 sequence encoding a C-terminal portion of the g3 protein, were amplified separately. The two fragments were combined in a shuttle vector and subsequently cloned into the phage genome. To distinguish the resulting constructs from the D3 helper phage described in example 3, the generally accepted alternative nomenclature for the g3 domains was used, in which D1, D2 and D3 are named N1, N2 and CT, respectively. The use of SnaBIclon and Bamlead primers and VCSM13 as a template in a PCR reaction detailed above resulted in the formation of a PCR product containing the g3 leader sequence, with a native SnaBI site upstream and an introduced BamHI site downstream. The use of BamCT and PacIclon primers and VCSM13 as a template in a PCR reaction detailed above resulted in the formation of a PCR product containing the g3 CT domain, with an introduced BamHI site upstream and a native PacI site downstream. The use of BglN2 and PacIclon primers and VCSM13 as a template in a PCR reaction detailed above resulted in the formation of a PCR product containing the g3 N2 and CT domains, with an introduced BglII site upstream and a native PacI site downstream.
All PCR products were cloned into plasmid pCR4-TOPO using the TOPO TA Cloning Kit for Sequencing (Invitrogen) and the sequences of the inserts were checked. The pCR4-TOPO derivative containing the leader sequence was digested with NotI and BamHI, and the insert was isolated from agarose gel. The pCR4-TOPO derivative containing the CT domain was also digested with NotI and BamHI, and the vector fragment was isolated. The insert was ligated with the vector fragment, resulting in a pCR4-TOPO derivative containing the g3 gene in which the N1 and N2 domains are deleted. This plasmid and VCSM13 were both digested with SnaBI and PacI. After isolation, the plasmid insert was ligated with the VCSM13 vector fragment.
The sequence of the insert in the resulting phagemid, named CT and identical to D3 depicted in FIG. 7A, was checked. A comparable procedure was used to construct a phagemid lacking only the N1 domain. For this construct, the pCR4-TOPO derivative containing the N2 and CT domains was digested with NotI and BglII, and the vector fragment was isolated. The insert containing the leader sequence was ligated with the vector fragment (the cohesive ends of BglII and BamHI are compatible), resulting in a pCR4-TOPO derivative containing the g3 gene in which the N1 domain is deleted. This gene was sub-cloned to VCSM13 as described above and the sequence of the insert in the resulting phagemid, named N2CT, was checked. The VCSM13-derived helper phage genome N2CT is depicted schematically in FIG. 10.

Example 11

Figure 11:
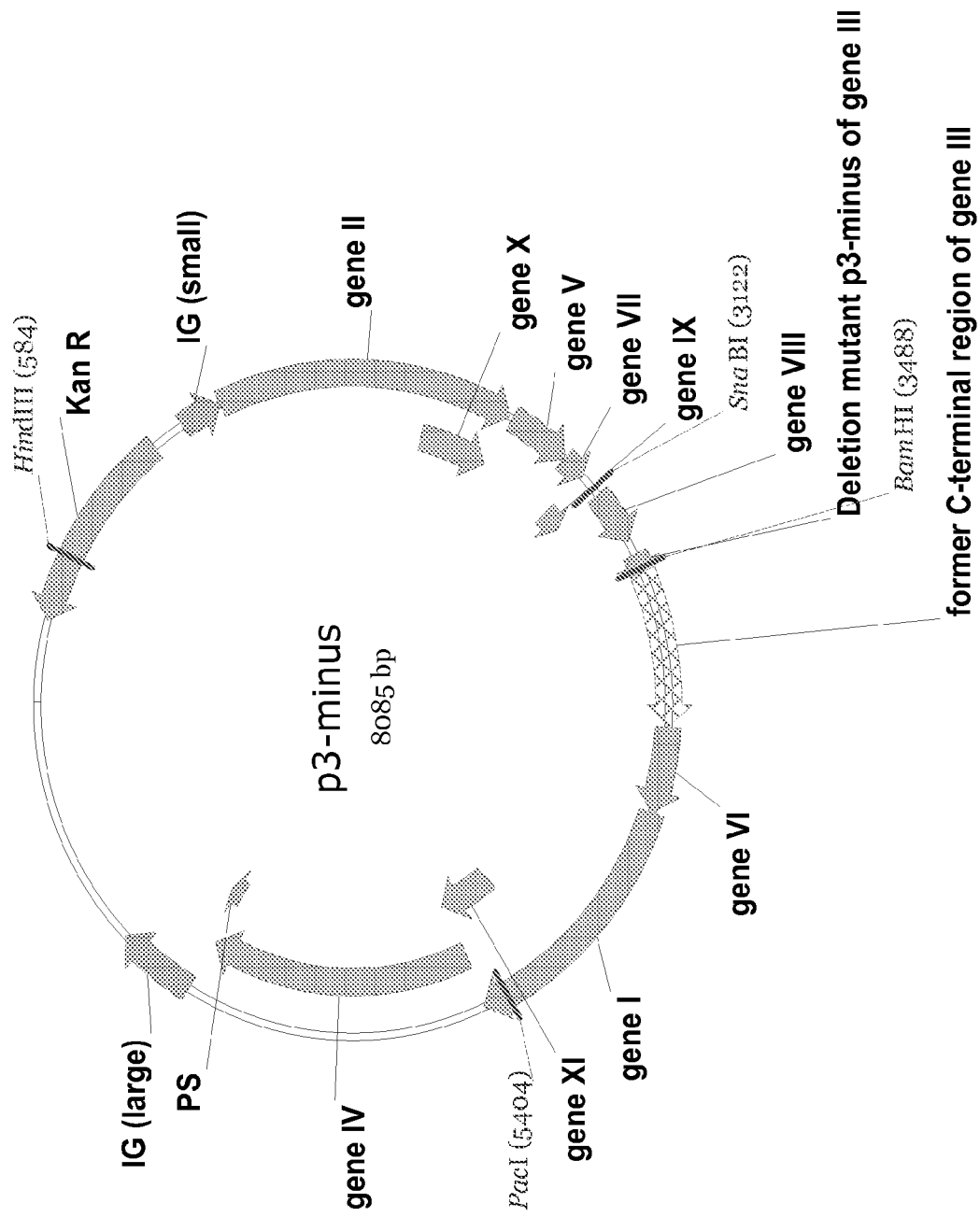
FIG. 11. Schematic representation of the VCSM13-derived p3-minus helper phage genome expressing the g3 leader followed by only seven amino acids. At the DNA level, a large part of the N2 (D2) domain and the entire CT (D3) domain are still present. The former C-terminal region of gene III is present, but does not encode functional protein through frame shift and therefore includes many in-frame stop codons.

Cloning of the P3-Minus Helper Phage Genome
In the cloning of the g3-minus helper phage genome described in example 2, almost the entire g3 sequence was deleted. The g3 gene overlaps the ribosome-binding site of the g6 gene and may contain other important features as well.
An alternative cloning strategy was applied, in which part of the N2 domain and the entire CT domain are retained at the DNA level, but a frame shift deletes these domains at the protein level. The pCR4-TOPO derivative containing the g3 leader fused to the g3 CT domain (see above) and VCSM13 were both cut with BamHI and SnaBI. After isolation from gel, the insert fragment of the pCR4-TOPO derivative, containing the g3 leader, was ligated with the vector fragment of VCSM13, containing a C-terminal portion of the N2 domain and the entire CT domain of g3. The sequence of the insert in the resulting phagemid, named p3-minus, was checked. In this construct, a frame shift occurs at the BamHI site located between the g3 leader and the C-terminal portion of the N2 domain, resulting in the introduction of over 30 stop codons downstream of the BamHI site. The VCSM13-derived helper phage genome p3-minus is depicted schematically in FIG. 11.

REFERENCES

Balint R F and Larrick J W (1993) Antibody engineering by parsimonious mutagenesis. Gene 137:109
Barbas C F, Hu D, Dunlop N, Sawyer L, Cababa D, Hendry R M, Nara P L, Burton DR (1994) In vitro evolution of a neutralizing human antibody to human Immunodeficiency virus type 1 to enhance affinity and broaden strain cross-reactivity. Proc Natl Acad Sci USA. 91:3809

Bass S H, Greene R and Wells J A (

What is claimed is:

1. A chimaeric phage displaying a mixture of proteins in its coat, said mixture of proteins comprising:
   a fusion protein comprising a proteinaceous molecule fused to the g3 phage coat protein; and
   a mutant form of said g3 phage coat protein,
wherein the D1 region, D2 region, or both the D1 and the D2 regions of the g3 protein are deleted from said mutant form of the g3 phage coat protein, wherein the mutant form comprises the D3 region, and wherein the chimaeric phage's genomic DNA sequences are based on the genomic sequences said phage of a M13, M13K07, VCSM13, or R408 phage.

2. The chimaeric phage of claim 1, further comprising a nucleic acid encoding said fusion protein.

3. The chimaeric phage of claim 1, wherein said proteinaceous molecule is selected from the group consisting of an antibody, a Fab fragment, a single chain Fv fragment, a variable region, a CDR region, and an immunoglobulin.

4. The chimaeric phage of claim 2, wherein expression of said fusion protein is under the control of a regulatable promoter.

5. The chimaeric phage of claim 4, wherein said promoter is selected from the group consisting of a AraC/BAD promoter, a psp promoter and a lac promoter.

6. A phage collection comprising the chimaeric phage of claim 1.

7. The phage collection of claim 6, wherein said phage collection is a phage display library.

8. A phage collection consisting essentially of chimaeric phages according to claim 1.

* * * * *

UNITED STATES PATENT AND TRADEMARK OFFICE
CERTIFICATE OF CORRECTION

PATENT NO.         : 7,901,919 B2
APPLICATION NO.    : 11/977954
DATED              : March 8, 2011
INVENTOR(S)        : Erwin Houtzager et al.

Page 1 of 1

It is certified that error appears in the above-identified patent and that said Letters Patent is hereby corrected as shown below:

On the title page:

| | |
|---|---|
| In ITEM (63) | insert after ITEM (62) and before ITEM (30) |
| Related U.S. Application Data | --Claims priority to Application No. 09/882,621, filed on June 15, 2001, now Patent No. 7,070,926.-- |

In the specification:

COLUMN 1,    LINES 16,17        change "both of which were filed" to --filed--

Signed and Sealed this
Ninth Day of April, 2013

Teresa Stanek Rea
*Acting Director of the United States Patent and Trademark Office*